United States Patent [19]

Dutta et al.

[11] Patent Number: 4,596,789

[45] Date of Patent: Jun. 24, 1986

[54] PROLINE DERIVATIVES

[75] Inventors: Anand S. Dutta, Stockport, England; Ross L. Stein, Wilmington, Del.; Diane A. Trainor, Glen Mills, Pa.; Richard A. Wildonger, Newark, Del.

[73] Assignees: ICI Americas Inc., Wilmington, Del.; Imperial Chemical Industries PLC, London, United Kingdom

[21] Appl. No.: 603,408

[22] Filed: Apr. 24, 1984

[30] Foreign Application Priority Data

Apr. 27, 1983 [GB] United Kingdom ................ 8311423
May 27, 1983 [GB] United Kingdom ................ 8314708

[51] Int. Cl.$^4$ ..................... A61K 37/00; C07C 103/52
[52] U.S. Cl. ...................................... 514/18; 530/330
[58] Field of Search .................... 260/112.5 R; 514/18

[56] References Cited

U.S. PATENT DOCUMENTS 3,935,280 1/1976 Lane .................................... 260/618
4,316,889 2/1982 Bajusz et al. ......................... 424/177

FOREIGN PATENT DOCUMENTS 880844 12/1979 Belgium.
2104082 3/1983 United Kingdom.

OTHER PUBLICATIONS

Biochemistry, 12, (1973) 4750–4755.
Chem. Abstr., vol. 90, (1979) 99132n.
Chem. Abstr., vol. 85, (1976) 105947x.
Chem. Abstr., vol. 92, (1980) 53952t.
Yasutake et al, "Reactivity of Human Leukocyte Elastase and Porcine Pancreatic Elastase Toward Peptide 4-Nitroanilides Containing Model Desmosine Residues, Evidence That Human Leukocyte Elastase is Selective for Cross-Linked Regions of Elastin"; Biochemistry, vol. 20, pp. 3675–3679 (1981).
Thompson et al, "Reaction of Peptide Aldehydes with Serine Proteases, Implications for the Entropy Changes Associated with Enzymatic Catalysis"; Biochemistry, vol. 18, pp. 1552–1558 (1979).
Thompson, Methods in Enzymology, vol. 46, pp. 220–225 (1977).
Thompson et al, Proceedings of the National Academy of Sciences (U.S.), vol. 67, pp. 1734–1740 (Dec. 1970).
Thompson et al, "Elastase-Catalyzed Amide Hydrolysis of Tri- and Tetrapeptide Amides, Biochemistry, vol. 12, pp. 66–71 (1973).
Thompson et al, "Dependence of the Kinetic Parameters for Elastase-Catalyzed Amide Hydrolysis on the Length of Peptide Substrates", Biochemistry, vol. 12, pp. 57–65 (1973).
Thompson et al, "Peptide Chloromethyl Ketones as Irreversible Inhibitors of Elastase", Biochemistry, vol. 12, pp. 44–47 (1973).
Thompson et al, "Restrictions on the Binding of Proline-Containing Peptides to Elastase", Biochemistry, vol. 12, pp. 51–57 (1973).
Brayer et al, "Crystallographic and Kinetic Investigations of the Covalent Complex Formed by a Specific Tetrapeptide Aldehyde and the Serine Protease from Streptomyces griseus", Proceedings of the National Academy of Sciences (U.S.), vol. 76, pp. 96–100 (Jan. 1979).
Thompson et al, "Evidence for an Extended Active Center in Elastase", Proceedings of the National Academy of Sciences, vol. 67, pp. 1734–1740 (Dec. 1970).
Powers, "Synthetic Elastase Inhibitors: Prospects for Use in the Treatment of Emphysema", American Review of Respiratory Disease; Supplement: Proteases and Antiproteases in the Lung, vol. 127, pp. S54–S58 (Feb. 1983).
Nakajima et al, "Mapping the Extended Substrate Binding Site of Cathepsin G and Human Leukocyte Elastase", Journal of Biological Chemistry, vol. 254, pp. 4027–4031 (May 1979).
Teshima et al, "A New Class of Heterocyclic Serine Protease Inhibitors", Journal of Biological Chemistry, vol. 257, pp. 5085–5091 (May 1982).
Mancuso et al, "Oxidation of Long-Chain and Related Alcohols to Carbonyls by Dimethyl Sulfoxide Activated by Oxalyl Chloride", J. Org. Chem., vol. 43, pp. 2480–2482 (1978).
Ho et al, "A Calorimetric Study of the Interactions Between Phosphorylase b and Its Nucleotide Activators"; Biochemistry, vol. 12, pp. 4750–4755 (1973).
Bajusz, et al, "Inhibition of Thrombin and Trypsin by Tripeptide Aldehydes"; Int, J. Peptide Protein Res., vol. 12, pp. 217–221 (1978).
Breaux, et al, "The Binding of Specific and Non-Specific Aldehyde Substrate Analogs to α-Chymotrypsin"; FEBS Letters, vol. 56, pp. 81–84 (1975).
Ito, et al, "Peptide Aldehydes Inhibiting Chymotrypsin"; Biochemical and Biophysical Research Communications, vol. 49, pp. 343–349 (1972).
Bajusz, et al, "Peptide Aldehyde Inhibitors of the Fibrinogen-Thrombin Reaction"; Peptides: Chemistry, Structure, Biology, vol. 4, pp. 603–608 (1975).
Westerik, et al, "Aldehydes as Inhibitors of Papain"; Journal of Biological Chemistry, vol. 247, pp. 8195–8197 (1972).
Thompson, "Use of Peptide Aldehydes to Generate Transition-State Analogs of Elastase"; Biochemistry, vol. 12, pp. 47–51 (1973).

Primary Examiner—Delbert R. Phillips
Attorney, Agent, or Firm—Rosemary M. Miano

[57] ABSTRACT

Proline derivatives of the formulae:

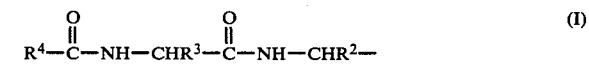

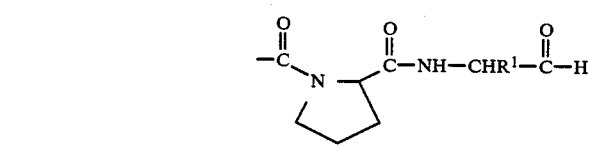

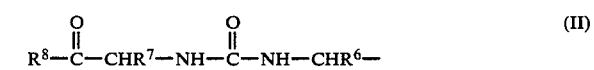

(Abstract continued on next page.)

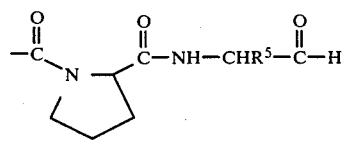

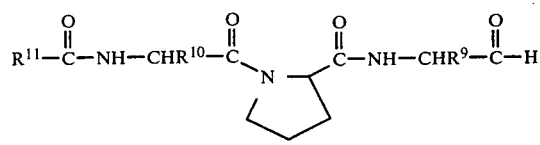

wherein $R^1$ through $R^{11}$ have defined values, and acid- and base-addition salts thereof, and equilibrium addition compounds of the aldehyde group thereof; processes for their preparation; pharmaceutical compositions; and intermediates for preparing said proline derivatives. The proline derivatives are human leukocyte elastase inhibitors which are useful, for example, in treating pulmonary emphysema.

16 Claims, No Drawings

PROLINE DERIVATIVES

BACKGROUND OF THE INVENTION

1. Field of the Invention

The present invention comprises certain proline derivatives which are useful as human leukocyte elastase inhibitors, e.g. in the treatment of tissue degenerative diseases such as pulmonary emphysema, atherosclerosis, rheumatoid and osteo arthritis in humans, methods for their use, processes used for their synthesis, intermediates useful in such syntheses and pharmaceutical compositions prepared with such derivatives.

2. Description of the Prior Art

Peptide aldehyde inhibitors of both porcine pancreatic elastase (PPE) and human leukocyte elastase (HLE) have been previously reported. For example, Thompson, Biochemistry, 1973, vol. 12, pages 47–51 has described the synthesis of two peptide aldehyde inhibitors of porcine pancreatic elastase. One of these was N-acetyl-L-alanyl-L-prolyl-L-alaninal.

Szabo et al., Acta Biochimica et Biophysica Academiae Scientiarum Hungaricae, 1982, vol. 17 (1-2), page 98, reports the synthesis of five peptide aldehyde compounds, all of which proved to be inhibitors for pancreatic elastase and human leukocyte elastase. The most potent HLE inhibitor reported was N-succinyl-D-phenylalanyl-L-prolyl-L-valinal; this compound produced 10–100 times stronger inhibition ($K_i = 4 \times 10^{-5}$) than the other four aldehydes.

Although various peptide aldehydes have been reported in the literature, none has been found to be clinically useful in the treatment of any tissue degenerative disease to date.

It is generally accepted that proteolysis of lung elastin by elastases, such as human leukocyte elastase (HLE) and cathepsin G, which are released from the granular fraction of polymorphonuclear leukocytes, is responsible for a major part of the tissue degradation seen in pulmonary emphysema. It is also believed that elastases are similarly involved in the initiation and progression of various other tissue degenerative diseases, such as atherosclerosis, osteo-arthritis and rheumatoid arthritis. Accordingly, the potent elastase inhibitors of this invention may be used in the treatment and/or prevention of any one or more of the above mentioned diseases. They may also be used as research tools in pharmacological and related studies.

SUMMARY OF THE INVENTION

The proline derivatives of the invention are of the following formulas (I), (II) or (III):

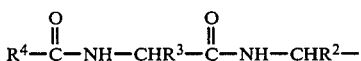
(I)

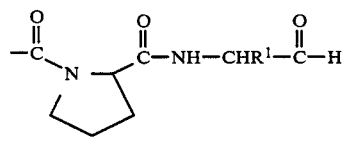

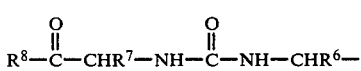
(II)

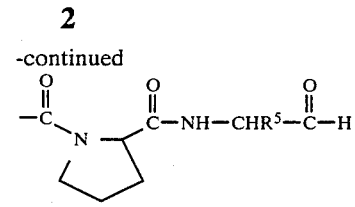

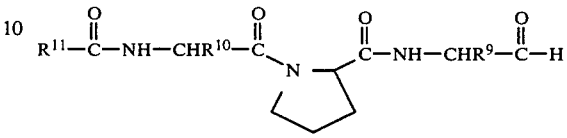
(III)

wherein $R^1$, $R^5$ and $R^9$ are lower alkyl groups containing from 3 to 6 carbon atoms;

$R^2$, $R^3$, $R^6$, $R^7$ and $R^{10}$ are alkyl groups of 1 to 10 carbon atoms which may optionally be substituted by a monocyclic aryl group or by an amide, urea or carbamate group via the nitrogen thereof;

$R^4$ and $R^{11}$ are lower alkyl, substituted lower alkyl, lower alkoxy or substituted lower alkoxy groups wherein the alkyl or alkoxy contains 1 to 6 carbon atoms, or monocyclic or bicyclic aryl groups; and $R^8$ is hydroxy, a lower alkoxy group containing 1 to 6 carbon atoms, or an aralkoxy group containing 7 to 12 carbon atoms;

and wherein —CHR$^2$—, —CHR$^3$—, —CHR$^6$—, —CHR$^7$—, —CHR$^{10}$— and the proline group are of the L-configuration; or a pharmaceutically-acceptable acid- or base-addition salt thereof or an equilibrium addition compound of the aldehyde group thereof.

The compounds of this invention of the formulas (I), (II) and (III) are highly potent, reversible, selective, competitive inhibitors of human leukocyte elastase (HLE). These compounds are up to 40,000 times more potent than the most potent aldehyde HLE inhibitors described in the prior art; see Szabo et al. cited above in this regard, and are useful in the treatment and/or prevention of tissue-degenerative diseases such as emphysema, atherosclerosis, osteo-arthritis and rheumatoid arthritis.

Also part of the present invention are processes for preparing compounds of the formula (I), (II) or (III); pharmaceutical compositions containing one or more compounds of the formula (I), (II) or (III) and a pharmaceutically acceptable diluent or carrier; methods for the treatment of pulmonary emphysema, atherosclerosis or osteo- or rheumatoid arthritis in a warm-blooded animal in need of such treatment which comprises administering to said animal a pharmaceutically effective amount of such composition; and intermediates used in the synthesis of compounds of the formula (I), (II) or (III).

DETAILED DESCRIPTION

The compounds of the formulas (I) and (II) are tetrapeptide aldehydes, and the compounds of the formula (III) are tripeptide aldehydes.

$R^1$, $R^5$ and $R^9$ may be straight or branched chain lower alkyl of 3 to 6 carbon atoms. Specific examples include n-propyl, iso-propyl, sec-butyl and iso-butyl. Preferred groups $R^1$, $R^5$ and $R^9$ are alpha branched chain lower alkyl groups of 3 or 4 carbon atoms such as isopropyl and sec-butyl.

$R^2$, $R^3$, $R^6$, $R^7$ and $R^{10}$ may be straight or branched chain alkyl groups of 1 to 10 carbons, e.g., 3 to 6 carbons, which may be substituted, e.g., at the terminal of a straight chain alkyl, by a monocyclic aryl group or by an amide, urea or carbamate group via the nitrogen atom thereof. Examples include n-propyl, iso-propyl, n-butyl, sec-butyl or isobutyl with substitutions including benzyl, benzyloxycarbonylamino, phenylaminocarbonylamino and pyridylcarbonylamino, e.g., 2-pyridylcarbonylamino.

Preferred groups $R^2$, $R^6$ and $R^{10}$ are alpha branched chain lower alkyl radicals of 3 to 6 carbon atoms such as isopropyl or sec-butyl, or an aralkyl radical having 7 to 12 carbon atoms such as benzyl.

Preferred groups $R^3$ are (a) straight or branched chain lower alkyl radicals of 3 to 6 carbon atoms such as n-propyl, isopropyl, n-butyl, sec-butyl or isobutyl; (b) aralkyl radicals of 7 to 12 carbon atoms such as benzyl; or (c) straight chain alkyl groups of 1 to 8 carbon atoms which are substituted by an amide, carbamate or urea group via the nitrogen atom thereof. Substituted alkyl radicals (c) may be represented by the formula

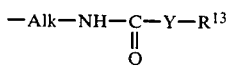

where Alk is a lower alkylene radical of 1 to about 8 carbon atoms, Y is a direct link, —O— or —NH— (corresponding to amide, carbamate and urea substituents, respectively), and $R^{13}$ is lower alkyl, aryl, aralkyl, or pyridyl. Examples of substituted alkyl radicals (c) include benzyloxycarbonylamino, phenylaminocarbonylamino (i.e., phenylureido), and 2-pyridylcarbonylamino.

Either $R^2$ or $R^3$ (and similarly $R^6$ and $R^7$) but preferably not both, can be amide-, carbamate-, or urea-substituted lower alkyl.

$R^4$ and $R^{11}$ may be: (a) lower alkyl such as methyl or tert.-butyl; (b) substituted lower alkyl, such as 2-carboxyethyl, 2-methoxycarbonylethyl, acetamidomethyl, and 2-methanesulfonamidocarbonylethyl; (c) lower alkoxy, such as tert.-butoxy; (d) substituted lower alkoxy such as benzyloxy, 2-(2-pyridyl)ethyloxy, and 2-methanesulfonylethyloxy; and (e) aryl, such as phenyl, 2,4-dichlorophenyl, 2-carboxyphenyl, and 4-biphenylyl. The lower alkyl or lower alkoxy groups may have 1 to 6 carbon atoms, and substituted lower alkyl or lower alkoxy groups may have 1 to 6 carbon atoms exclusive of those in the substituents.

$R^8$ may be hydroxyl, lower alkoxy of 1 to 6 carbon atoms, or aralkoxy of 7 to 12 carbon atoms.

The preferred substituent $R^8$ in formula (II) compounds is lower alkoxy, such as methoxy.

The preferred substituent $R^{11}$ in formula (III) compounds is substituted lower alkyl, in particular carboxyalkyl such as 2-carboxyethyl, or alkyloxycarbonylalkyl such as methoxycarbonylethyl or alkoxy such as tert.-butoxy, or aralkoxy such as benzyloxy.

The equilibrium addition compounds of the aldehyde group of formulae (I), (II) or (III) include the bisulfites, hemiacetals and hemiaminals, as well as other masked aldehydes as described in "The Chemistry of the Carbonyl Group", Vol. 2 in the series "The Chemistry of Functional Groups", Ed. by S. Patai, Interscience Publishers, a division of John Wiley & Sons, New York (1970).

The bisulfite addition products are those in which the —CHO group is converted to a —CHOHSO$_3$H, e.g., by reaction with a sulfite, e.g., sodium hydrogen sulfite of the formula NaHSO$_3$. The reaction may be conducted by dissolving the aldehyde in a solvent such as aqueous methanol, adding an excess, e.g., a double molar amount, of sodium hydrogen sulfite, and removing the solvent.

The hemiacetals are formed by addition of one mole of a monohydric alcohol such as dodecanol to the —CHO group.

The hemiaminals are formed by addition of one mole of a primary amine such as lysine, or a secondary amine such as sarcosine (which is N-methylglycine) to the —CHO group. Addition may be carried out by dissolving the aldehyde in a suitable solvent such as methanol, adding the amine, and removing the solvent.

The salts of the compounds of formula (I), (II) and (III) include pharmaceutically-acceptable base- or acid-addition salts such as with a mineral acid, e.g., hydrochloric, or an organic acid such as citric, maleic, fumaric or acetic. Base-addition salts include those with alkali metal hydroxides such as sodium hydroxide, alkaline earth hydroxides and organic amine salts. Such salts may be prepared by dissolving the proline derivative in a mixture of water and a water-miscible organic solvent, adding an aqueous solution of the base and recovering the salt in the aqueous solution.

The compounds of the present invention are of the L-configuration at all chiral centers except optionally the point of attachment of the $R^1$, $R^5$ or $R^9$ group. The configuration at $R^1$, $R^5$ and $R^9$ can be D, L, or a mixture thereof. Preferably the compounds of this invention are of the L-configuration at all chiral centers including the point of attachment of the $R^1$, $R^5$ or $R^9$ group. The L-configuration at the point of attachment of $R^2$, $R^6$ or $R^{10}$ is particularly important, since the compounds of this invention, which have this configuration, are far more active (approximately 100 times more active) than the isomers having the D-configuration at this location. The term, "L-configuration" herein denotes a steric configuration which is the same as that in the closest naturally occurring L-amino acids.

Compounds of the formula (I) and their pharmaceutically-acceptable acid- and base-addition salts and aldehyde adducts constitute a preferred group of compounds. Especially desirable are formula (I) compounds having the L-configuration at all chiral centers.

Preferred compounds, all of which are of the formula (I), and of the L-configuration at all chiral centers, are the following:

(a) N-alpha-succinyl-N-epsilon-benzyloxycarbonyl-L-lysyl-L-valyl-L-propyl-L-valinal, (b) N-acetylglycyl-N-epsilon-benzyloxycarbonyl-L-lysyl-L-valyl-L-propyl-L-valinal, (c) N-benzyloxycarbonyl-L-norleucyl-L-valyl-L-propyl-L-valinal, (d) N-alpha-[3-(methylsulfonylaminocarbonyl)propionyl]-N-epsilon-benzyloxycarbonyl-L-lysyl-L-valyl-L-propyl-L-valinal, (e) N-alpha-succinyl-N-epsilon-benzyloxycarbonyl-L-lysyl-L-phenylalanyl-L-prolyl-L-valinal, (f) N-alpha-(2,4-dichlorobenzoyl)-N-epsilon-benzyloxycarbonyl-L-lysyl-L-valyl-L-prolyl-L-valinal, (g) N-alpha-glutaryl-N-epsilon-benzyloxycarbonyl-L-lysyl-L-valyl-L-propyl-L-valinal, (h) N-alpha-succinyl-N-epsilon-(2,4-dichlorobenzoyl)-L-lysyl-L-valyl-L-propyl-L-valinal, and (i) N-alpha-(4-phenylbenzoyl)-N-epsilon-benzyloxycarbonyl-L-lysyl-L-valyl-L-propyl-L-valinal.

and the pharmaceutically-acceptable acid- and base-addition salts thereof and the pharmaceutically-acceptable equilibrium addition compounds of the aldehyde group thereof. Compounds (b) through (f) are especially preferred, and compound (a) is the most highly preferred.

The aldehydes of the formula (I), (II) or (III) can be prepared by oxidation of the corresponding alcohol or by hydrolysis or transacetalization of the corresponding acetal (or more broadly, by removal of an aldehyde protecting group from an aldehyde derivative having such group). The alcohols and acetals (or other derivatives having an aldehyde protecting group) in turn can be prepared according to peptide synthesis techniques which are known in the art.

The alcohols are compounds of the following formulas (I-A), (II-A) and (III-A):

Aldehyde derivatives of the compounds of formulas (I), (II) and (III) in which the —CHO group is replaced by an aldehyde protecting group are compounds of the following formulas (I-B), (II-B), and (III-B):

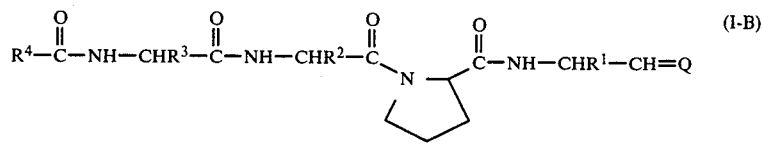

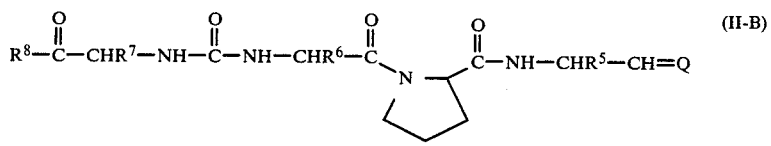

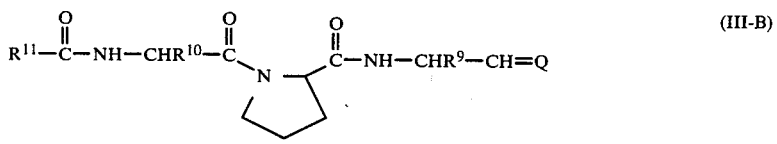

where Q is an aldehyde protecting group and $R^1$ and $R^{11}$ are as previously defined. The preferred aldehyde protecting group Q is the acetal, in which case Q is $(OR^{12})_2$ where $R^{12}$ is lower alkyl of 1 to 6 carbon atoms or (in the case of an acetal formed from a diol such as ethylene glycol or propylene glycol) the two groups $R^{12}$ together with the adjacent oxygens and the carbon to which they are attached form a 5- or 6-member heterocyclic (i.e., alkylenedioxy) ring. Alternatively, the protecting group may be a thioacetal, in which case Q is $(SR^{12})_2$ where $R^{12}$ has the meanings stated above.

The acetals are compounds of the following formulas (I-C), (II-C) and (III-C):

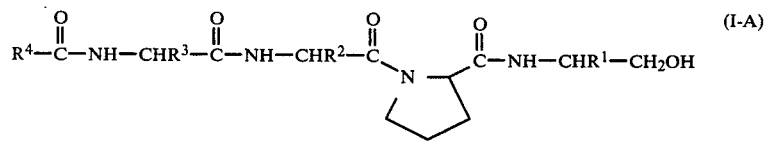

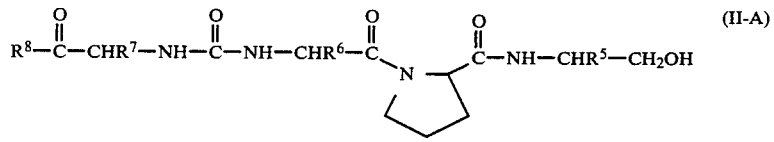

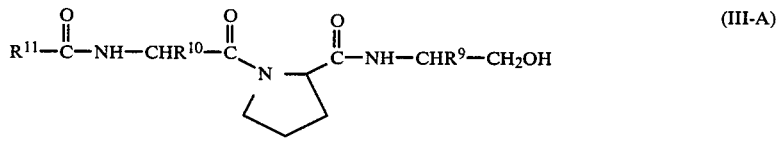

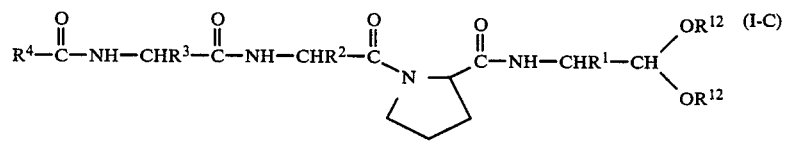

-continued

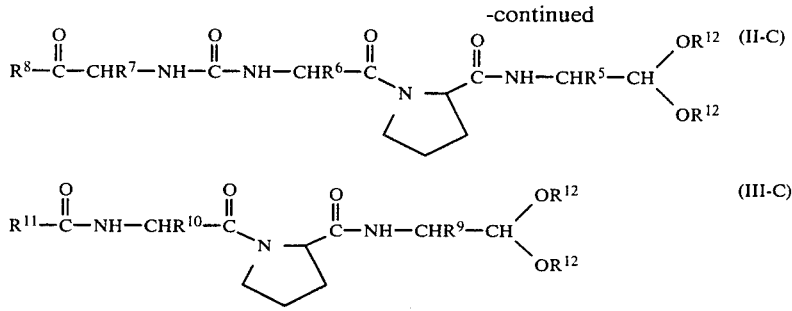

where $R^1$ to $R^{12}$ are as previously defined.

Compounds of the invention of formulas (I), (II) and (III) can be prepared by oxidation of the corresponding alcohol of the formula (I-A), (II-A) or (III-A). This oxidation can be accomplished by any of several procedures including:

(a) Swern modification of a Moffatt oxidation in which the alcohol is reacted at low temperature (−78° to −20° C.) with a reagent prepared in situ by reaction of dimethyl sulfoxide (DMSO) with an activating agent such as oxalyl chloride or trifluoroacetic anhydride at low temperature in a solvent such as dichloromethane ($CH_2Cl_2$). This procedure is described, for example, by A. J. Mancuso et al. in the Journal of Organic Chemistry, Vol. 43, No. 12, pages 2480–2482 (1978) and Vol. 44, No. 23, pages 4148–4150 (1979).

(b) a Collins oxidation in which the alcohol is reacted with a mixture of chromium trioxide ($CrO_3$) and pyridine at low temperature (−40° to −20° C.) in a solvent such as dichloromethane.

(c) oxidation by other chromium reagents such as pyridinium chlorochromate at temperatures from −20° C. to 25° C. in solvents such as dichloromethane.

Alternatively, compounds of the invention of the formulas (I), (II) and (III) can be prepared by removing the protecting group Q from a corresponding protected compound of the formula (I-B), (II-B) or (III-B). Thus, for example, compounds of the invention of formulas (I), (II) and (III) can be prepared by hydrolysis of the corresponding acetal of the formula (I-C), (II-C) or (III-C). This hydrolysis may be carried out in the presence of an acid in a mixed aqueous-organic solvent medium. The medium may be a mixture of water and one or more water-miscible organic solvents such as methanol, tetrahydrofuran (THF), or acetone. The medium may be acidified with an acid such as hydrochloric acid, p-toluenesulfonic acid or a strongly acidic ion exchange resin such as Dowex ® 50Wx8-H (Dowex ® is a registered trademark of The Dow Chemical Company, Midland, Mich., U.S.A.). Alternatively, the acetal can be removed in a trans-acetalization reaction in the presence of excess acetone or other low molecular weight ketones in the presence of an acid catalyst such as p-toluene-sulfonic acid or a strongly acidic ion exchange resin such as Dowex ® 50Wx8-H.

Compounds of the formulas (I-A), (II-A), (III-A), (I-B), (II-B), (III-B), (I-C), (II-C) and (III-C) are novel intermediates.

Both the alcohols of formulas (I-A), (II-A) and (III-A) and the aldehyde derivatives (e.g., acetals) of formulas (I-B), (II-B) and (III-B) can be made from readily available materials by peptide synthesis methods which are known in the art. Basically, these consist of peptide coupling and protection and deprotection reactions (to protect and deprotect amino and carboxy groups), arranged in a sequence which will give the desired peptide compound.

Peptide coupling may be represented generally by equation (1) below:

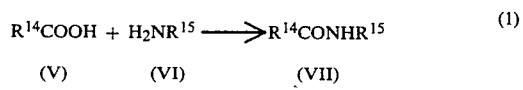

where $R^{14}$ and $R^{15}$ are amino acid or peptide residues. In other words, both (V) and (VI) represent amino acids or peptides. As applied to the present invention, the maximum number of peptide units in compound (VII) is either 3 or 4.

These peptide coupling procedures can be carried out by any one of several procedures which are known in the art.

For example, coupling can be accomplished in the presence of dicyclohexylcarbodiimide or 1-(3-dimethylaminopropyl)-3-ethylcarbodiimide hydrochloride and 1-hydroxybenzotriazole and a base such as triethylamine or N-methylmorpholine in a solvent such as tetrahydrofuran or dimethylformamide. Preferably the coupling is carried out at a temperature of from 0° to room temperature.

Alternatively, another example of the coupling procedure is the reaction of Equation (1) in which the carboxylic acid reactant is first activated by formation of a mixed anhydride, for example a mixed carbonic anhydride. This anhydride can be prepared by reacting a carboxylic acid with, for example, isobutyl chloroformate or ethyl chloroformate in the presence of an amine such as triethylamine or N-methylmorpholine in a solvent such as tetrahydrofuran or dichloromethane at a temperature from −20° to 0° C. The mixed anhydride is then reacted with the amine component of Equation (1) in the same solvent in the presence of the same amine at temperatures from −40° C. to room temperature to provide the coupled product.

In some cases the acid (V) of equation (1) can be reacted in the form of its acid halide or acid anhydride derivative with the amine (VI) in the presence of a tertiary amine such a N-methylmorpholine or triethylamine in solvents such as tetrahydrofuran or dichloromethane at a temperature of from −20° C. to room temperature. Alternatively, the acid chloride can be reacted with the amine in an aqueous solution containing sodium hydroxide. In some instances a water-immiscible solvent such as ether or dichloromethane is present. The reaction is conducted at temperatures of −10° C. to room temperature.

Other free amino groups or free carboxylic acid groups in the reacting compounds (V) and (VI) must sometimes be temporarily protected during the coupling reaction for the coupling to proceed in the desired manner. These protecting groups, methods for their introduction, and methods for their removal are known in the art. The protecting groups are chosen so that they may be selectively introduced and removed under conditions which do not affect other reactive groups in the compounds.

Examples of amino protecting groups are tert-butyloxycarbonyl, which may be removed by anhydrous acid such as trifluoroacetic acid or hydrogen chloride in a solvent such as ether, ethyl acetate or dichloromethane; benzyloxycarbonyl, which may be removed by catalytic hydrogenolysis in the presence of a catalyst such as palladium on carbon in a solvent such as ethanol or ethyl acetate; and methylsulfonylethyloxycarbonyl, which may be removed by treatment with a base such as sodium hydroxide in a solvent such as aqueous methanol or tetrahydrofuran.

Acid protecting groups include the methyl ester, which may be removed by basic hydrolysis in the presence of sodium hydroxide or sodium carbonate in a solvent such as aqueous tetrahydrofuran or methanol; the tert-butyl ester, which may be removed in the presence of acids such as hydrogen chloride or trifluoroacetic acid in a solvent such as ether, ethyl acetate or dichloromethane; and the benzyl ester, which may be removed by basic hydrolysis as above or by catalytic hydrogenolysis as described above. These protecting groups can be removed immediately after a coupling reaction or left in place until a later stage in the synthesis and removed at that time.

Various methods can be used to prepare alcohols of the formula (I-A). The following are illustrative.

A first method for preparing alcohols of formula (I-A) involves reacting compounds of the following formulae (VIII) and (IX) to produce (X):

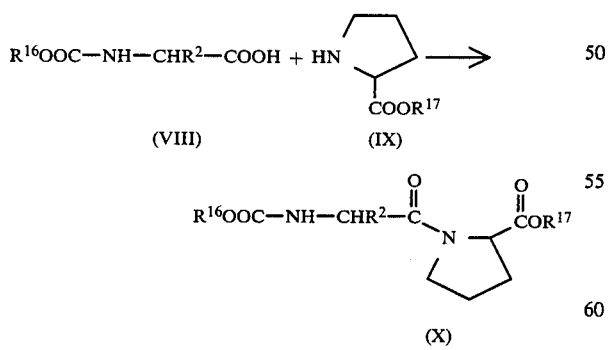

(VIII)    (IX)

(X)

wherein $R^{16}$ and $R^{17}$ are arylalkyl or alkyl groups, e.g., benzyl, methyl or tert-butyl. For example, the coupling is conducted in the presence of coupling promoters such as dicyclohexylcarbodiimide (DCC) and 1-hydroxybenzotriazole (HOBT) or by the mixed anhydride procedure with isobutyl chloroformate. Unless otherwise indicated, the definitions of the various R groups throughout the specification are as defined previously. The —COOR$^{16}$ protecting group is then removed by catalytic hydrogenolysis or acid-catalyzed deprotection with concentrated mineral acid or a strong organic acid such as trifluoroacetic acid, and the free base or salt is reacted with an acid of the formula (XI) to produce a compound of formula (XII):

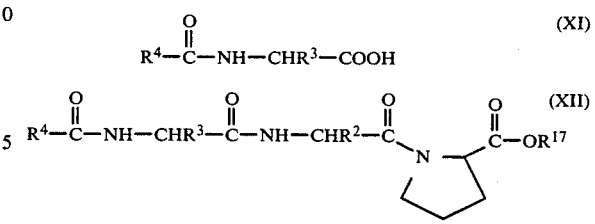

at about 0° C. to room temperature. From the ester of formula (XII), the OR$^{17}$ group is replaced by —OH by saponification with NaOH at about room temperature or via catalytic hydrogenolysis and this carboxylic acid is reacted with an aminoalcohol of the formula (XIII) to produce the compound of the following formula (I-A):

$$H_2N-CHR^1-CH_2OH \quad (XIII)$$

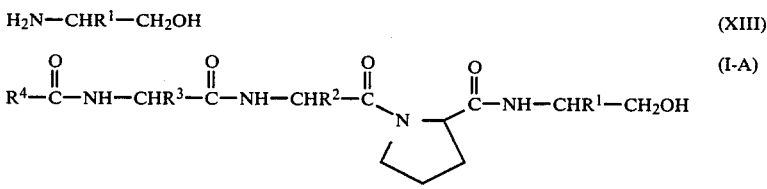

at a temperature of about −40° to −23° C. In the coupling reaction to produce (I-A), isobutyl chloroformate is used to produce a mixed carbonic anhydride of the carboxylic acid of the ester (XII) in the presence of N-methylmorpholine. Compounds of the formula (XIII) may be produced from the corresponding aminoacid of the formula $H_2N-CHR^1$-COOH by first esterifying the acid with an alcohol such as methanol or ethanol, to produce the aminoester of the formula $H_2N-CHR^1-COOR^{18}$ where $R^{18}$ is an alkyl group of 1 to 2 carbons, and reducing the aminoester with a reducing agent such as lithium aluminum hydride to yield (XIII), $H_2N-CHR^5-CH_2OH$ or $H_2N-CH-R^9-CH_2OH$. The alcohol of formula (I-A) may be oxidized to produce a compound of formula (I) as described above.

A second method for preparing formula (I-A) compounds involves reacting the formula (XI) acid with an amine of formula (XIV) to produce a compound of formula (XV):

$$(XI) + H_2N-CHR^2-COOR^{19} \longrightarrow$$
$$(XIV)$$

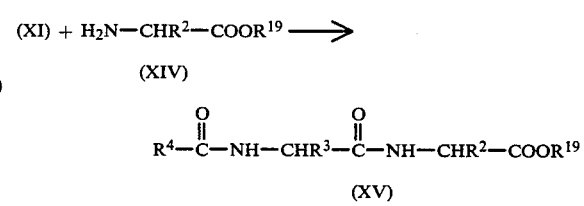

(XV)

wherein $R^{19}$ is an alkyl or arylalkyl group, e.g. methyl, at a temperature of about −40° to −20° C., e.g., using N-methylmorpholine and isobutyl chloroformate as described previously. The formula (XV) ester is then saponified by reaction with an alkali metal hydroxide at about room temperature and the acid is reacted with a compound of formula (IX) to yield formula (XII) which may then be taken on to (I-A) and (I) as described above.

A third method of preparing formula (I-A) compounds involves changing the substitution on the $R^2$ or $R^3$ alkyl groups. It should be noted that such change may also take place in preparing compounds of the invention of formulas (II-A) and (III-A). Thus, a compound of formula (XII) wherein at least one of $R^2$ or $R^3$ is substituted alkyl may be reacted to give the corresponding amine of the formula (XVI):

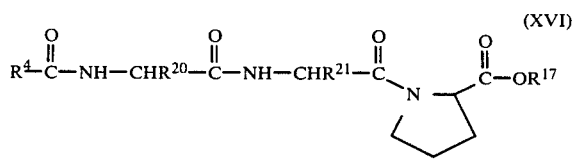

(XVI)

wherein at least one of $R^{20}$ and $R^{21}$ is an alkyl group of 1 to 10 carbons substituted by a —$NH_2$ under conditions as described herein for the removal of a —$COOR^{16}$ group, in particular if the substitution is a carbamate. The amine (XVI) may then be either reacted with a carboxylic acid to produce a compound of formula (XII) wherein the $R^2$ and/or $R^3$ which had been alkyl substituted by carbamate is transformed into an alkyl substituted by an amide, or reacted with an isocyanate to produce a compound of formula (XII) wherein the $R^2$ and/or $R^3$ which had been alkyl substituted by carbamate is transformed into an alkyl substituted by a urea moiety. Both of such formula (XII) compounds may be saponified and then condensed with a compound of formula (XIII) to produce compound (I-A).

In some instances the synthetic methods used to produce compounds (I), (II) and (III) involve substitution of one $R^4$, $R^8$ or $R^{11}$ group for another in compounds (I-A), (II-A) and (III-A). For example, when it is desired to substitute a carboxyalkyl group for a tert-butoxy group in compounds of formulas (I-A) and (III-A), the tert-butoxy group is removed by acid catalyzed deprotection, e.g., with trifluoroacetic acid, and the resulting amine is reacted with a monoester-acid chloride or anhydride such as succinic, glutaric or adipic anhydride (e.g., at room temperature in acetonitrile) to produce a second compound of the formula (I-A) or (III-A), in which $R^4$ or $R^{11}$ is carboxyalkyl (e.g., carboxyethyl), alkoxycarbonylalkyl, aryloxycarbonylalkyl, or aralkoxycarbonylalkyl. The second compound (I-A), (II-A) or (III-A) may then be oxidized to the corresponding compound (I), (II) or (III).

Compounds of the formula (II-A) may be produced by preparing a compound of the formula (X) from compounds of formulas (VIII) and (IX) as explained above, removing the —$COOR^{16}$ protecting group and reacting the free base or salt with an isocyanate of the formula (XVII) to produce the urea of the following formula (XVIII):

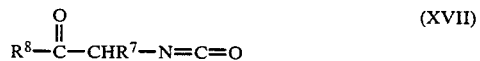

(XVII)

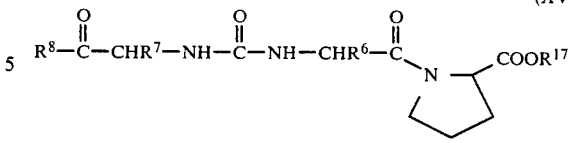

(XVIII)

by reaction at 0° C. to room temperature. The isocyanate of formula (XVII) may be prepared from the corresponding aminoacid ester of the formula $R^8$—CO—$CHR^7$—$NH_3^+Cl^-$ by reaction with phosgene at a temperature of 115° C. The urea (XVIII) is then converted to the corresponding carboxylic acid, replacing $OR^{17}$ where $R^{17}$ is benzyl with OH by catalytic hydrogenolysis with a noble metal as the catalyst and hydrogen. The thus-produced carboxylic acid is then condensed with an aminoalcohol of the formula $H_2N$—CH-$R^5$—$CH_2OH$, as described above for the reaction of compound (XIII) to produce (I-A), to produce the compound of the formula (II-A). The compound of formula (II-A) is then oxidized to the desired product of formula (II) as described above.

Compounds of the formula (III-A) may be produced by condensing a compound of the formula (XI), wherein $R^3$ and $R^4$ are values of $R^{10}$ and $R^{11}$, respectively, with a compound of the formula (IX) to yield a compound of the following formula (XIX):

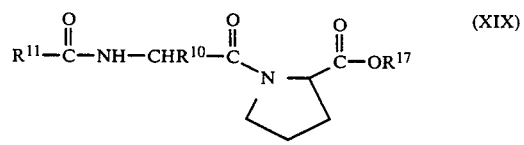

(XIX)

with DCC and HOBT as described for the coupling of (VIII) and (IX) to produce (X). The ester of formula (XIX) may then be cleaved by saponification or hydrogenolysis as described above for the reaction of (XII) to yield the corresponding acid. The acid is then condensed with an aminoalcohol of the formula $H_2N$—CH-$R^9$—$CH_2OH$, as described above for the preparation of compound (I-A) from (XII), to produce the compound of the formula (III-A). The compound of formula (III-A) is then oxidized to the desired product of formula (III) as described above.

Compounds of the formulas (I-B), (II-B) and (III-B) can also be prepared according to known peptide synthesis techniques. A preferred method for preparing acetals of the formula (I-C) will now be described for purposes of illustration.

According to a preferred method of preparing an acetal of the formula (I-C), a compound of the formula (VIII) is reacted with a compound (IX) to form a compound (X) as previously described. In particular, $R^{16}$ in formulas (VIII) and (X) may be benzyl. The —$COOR^{16}$ protecting group is removed, e.g., by catalytic hydrogenolysis, as described previously. The resulting free amine or salt is then reacted with a compound of the formula (XI) under known coupling conditions, e.g., at 0° C. to room temperature in the presence of coupling promoters such as DCC and HOBT, to produce a compound of the formula (XII). Preferably in formula (XII), $R^4$ is tert-butoxy and $R^{17}$ is tert-butyl. In this case, reaction of (XII) with trifluoroacetic acid results in replacement of —$OR^{17}$ with —OH and removal of $R^4CO-$. The resulting amine or acid addition salt is reacted with a suitable acylating agent containing $R^4$, e.g., a monoester-acid chloride of succinic acid, giving a compound of the following formula (XX):

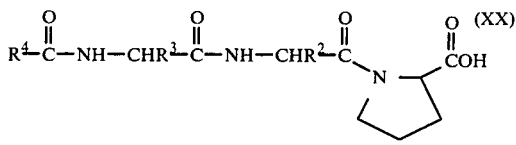

where $R^4$ is, for example, carboxyalkyl, alkyloxycarbonylalkyl or aralkyloxycarbonylalkyl.

An aminoalcohol of the formula (XIII) (e.g., L-valinol) is coupled with benzyl chloroformate at 0° to 25° C. to protect the amino group. The amino-protected derivative of (XIII) is then oxidized by means described earlier in this specification, e.g., by a Swern modification of a Moffatt oxidation, to give an aldehyde of the following formula (XXI):

where $R^{22}$ is lower alkyl or aralkyl, e.g., benzyl. Acid-catalyzed acetalization, e.g., with triethyl orthoformate in absolute alcohol acidified with p-toluenesulfonic acid at room temperature, yields an acetal (e.g., the diethyl acetal) of (XXI). The amine protecting group may be removed, e.g., by catalytic hydrogenolysis when $R^{22}$ is benzyl, to give an aminoacetal of the following formula (XXII):

Compounds (XX) and (XXII) are coupled under suitable coupling conditions, e.g., in the presence of isobutyl chloroformate at a temperature of $-40°$ C. to room temperature, to yield a compound of the formula (I-C). When $R^4$ is hydrolyzable under basic conditions, as for example when $R^4$ is alkoxycarbonylalkyl, the $R^4$ group may be converted to an alternate $R^4$ group by basic hydrolysis, for example, the conversion of methoxycarbonylethyl to carboxyethyl. Hydrolysis or transacetalization of (I-C) yields the desired compound (I).

The above synthesis is particularly useful for preparing N-alpha-succinyl-N-epsilon-benzyloxycarbonyl-L-lysyl-L-valyl-L-valinal, which is a highly preferred compound of the formula (I) of this invention.

Other reactants and sequences of steps can be used when it is desired to produce other compounds of the formula (I), (II) or (III) of this invention via the corresponding acetals.

According to a further feature of the invention there are provided pharmaceutical compositions comprising a pharmaceutically-effective amount of at least one proline derivative of the formula (I), (II) or (III), wherein $R^1$, $R^2$, $R^3$, $R^4$, $R^5$, $R^6$, $R^7$, $R^8$, $R^9$, $R^{10}$ and $R^{11}$ are as defined above, or a pharmaceutically-acceptable acid- or base-addition salt thereof, or a pharmaceutically-acceptable equilibrium addition compound of the aldehyde group thereof, and a pharmaceutically-acceptable diluent or carrier.

The potency of compounds of the invention to act as elastase inhibitors was determined by the ability of a compound of the invention to inhibit the action of human leukocyte elastase (HLE) on a low molecular weight peptide substrate. The potency of an inhibitor is evaluated by obtaining a kinetic determination of the dissociation constant, $K_i$, of the complex formed from the interaction of the inhibitor with HLE. The substrate used was the anilide methoxysuccinyl-alanyl-alanylprolyl-valine-p-nitroanilide as described by K. Nakajima et al. in The Journal of Biological Chemistry, Vol. 254, pages 4027-4032 (1979) and by T. Teshima et al. in The Journal of Biological Chemistry, Vol. 257, No. 9, pages 5085-5091 (1982). The HLE enzyme used in these studies may be obtained according to B. R. Viscarello et al. in Preparative Biochemistry, Vol. 13 (1983).

From HLE enzyme obtained as described in the Viscarello et al reference, a standard rate of production of p-nitroaniline was measured at room temperature spectrophotometrically in the visible spectrum at 410 nanometers, with automatic data acquisition in a Cary 210-Apple III Plus microcomputer system obtained from Varian Associates. Reactions were initiated by injection of a small aliquot (50 or 100 microliters) of a stock solution of the anilide substrate in DMSO into a cuvette containing buffer and HLE enzyme. The amount of HLE used is sufficient to produce an initial velocity of about 0.01 OD (optical density) per minute. Final volume was 3.0 ml. Initial velocities of production of p-nitroaniline were determined from linear regression analysis of at least 30 data points ($OD_{410}$ vs. time) taken during the initial, linear, portion of the reaction. The initial velocity for the HLE sample without any inhibitor being present was obtained and used as a standard for the subsequent determination of the initial velocity of the reaction in the presence of an inhibitor to be tested. The $K_i$ value of a particular inhibitor was determined as follows. To a 3 ml cuvette were added 2.78 ml of a buffer (9 millimolar sodium phosphate, 10% DMSO (v/v), pH=7.9), 100 microliters of inhibitor solution in DMSO and 20 microliters of HLE stock solution at the same concentration used in the control. After the inhibitor and enzyme solution had equilibrated, the reaction was initiated by the addition of 100 microliters of the stock substrate solution in DMSO. The final solution was 16.6% (v/v) in DMSO, with pH 8.1. The substrate was at an initial concentration of $1.6 \times 10^{-4}$ molar. Duplicate or triplicate runs were done at zero inhibitor concentration as controls and at least three non-zero inhibitor concentrations typically from $1 \times 10^{-5}$ M to $1 \times 10^{-8}$ M. A Dixon plot (reciprocal velocity vs. inhibitor concentration) was used to determine the $K_i$ as described by I. H. Segal in "Enzyme Kinetics", pages 109-111, John Wiley and Sons, New York (1975). Variation in the percent DMSO will result in small changes in the $K_i$ values. The $K_i$ value for the product of Example 32g was $9.4 \times 10^{-8}$ molar; Example 1f was $1.5 \times 10^{-8}$ molar; Example 5b was $3.0 \times 10^{-8}$ molar; and Example 8b was $6 \times 10^{-9}$ molar. Preferred compounds of this invention have Ki values in the range $10^{-9}$ molar to $10^{-7}$ molar.

Pharmacokinetics: Male Syrian hamsters (80 to 120) g) are injected subcutaneously with the test compound. Prior to injection and at varying time periods thereafter they are lightly anesthetized with ether and blood samples of approximately 0.2 ml each are withdrawn by cardiac puncture. The blood is expressed into 2 ml centrifuge tubes and allowed to clot for one hr. The sample is then centrifuged and the serum removed. Blood samples are taken before (time 0) and 15, 30, 60, 90 and 120 minutes after subcutaneous administration of the test compound in an appropriate vehicle.

Drug levels are determined by first inactivating endogenous elastase inhibitors by incubation of 50 microliters of serum with an equal volume of buffer containing 5 mg/ml bovine pancreatic trypsin for 5 min. The trypsin inactivated serum (40 microliters) is then added to a 3 ml cuvette containing buffer made 20 nM with respect to Human Leukocyte Elastase. After an additional 2 min. incubation, the reaction is started by the addition of substrate (100 microliters) (MeOSuc-Ala-Ala-Pro-Val-pNA, 1.6 mM) and the reaction monitored spectrophotometrically at a wavelength of 410 nm. Serum concentrations of the test compounds are determined by the following equation:

$$[I] = \left[ \frac{[E]}{V_o/V_i} + K_i \left(1 + \frac{[S]}{K_m}\right) \right] \left[ \frac{V_o}{V_i} - 1 \right]$$

where [I], [E] and [S] are the assay concentrations of inhibitor enzyme and substrate respectively, Ki is the inhibition constant of the inhibitor being assayed, Km is the Michaelis constant of the substrate, Vo is the control uninhibited reaction velocity, and Vi is the inhibited reaction velocity. Velocity of the time 0 serum reaction is taken as V. Data are expressed as molar concentration of inhibitor in serum vs time post inhibitor administration. An approximate serum half-life (t½) is calculated from the curve.

The compound N-alphasuccinyl-N-epsilon-benzyloxycarbonyl-L-lysyl-L-valyl-L-prolyl-L-valinal (the compound of examples 5 and 6) is highly preferred because, in addition to high potency as measured by its Ki value, this compound has good activity in animals as measured by the above test.

None of the invention compounds which have been tested in vivo exhibited any signs of toxicity at the concentrations administered (about 30 mg/kg of body weight).

The compounds of the present invention may be administered to an animal particularly a human in need thereof, for the alleviation of conditions including pulmonary emphysema, atherosclerosis and osteo and rheumatoid arthritis, in particular for emphysema. The mode of administration may be parenteral, including the subcutaneous deposit of an osmotic pump, or via a powdered or liquid aerosol. For parenteral administration, a 1 to 10 ml intravenous, intramuscular or subcutaneous injection would be given containing about 0.02 to 10 mg/kg of body weight of a compound of the invention 3 or 4 times daily. The injection would contain a compound of the invention in an aqueous isotonic sterile solution or suspension optionally with a preservative such as phenol or a solubilizing agent such as ethylenediaminetetraacetic acid (EDTA). In a powdered aerosol, compounds of the invention may be administered in the same manner as cromolyn sodium via a Spinhaler ® turbo-inhaler device obtained from Fisons Corp. of Bedford, Mass. at a rate of about 0.1 to 50 mg per capsule, 1 to 8 capsules being administered daily for an average human. Each capsule to be used in the Spinhaler ® contains the required amount of a compound of the invention with the remainder of the capsule being a pharmaceutically-acceptable carrier such as lactose. In a liquid aerosol, the compounds of the invention are administered at the rate of about 100 to 1000 micrograms per "puff" or activated release of a standard volume of propellant. The liquid aerosol would be given at the rate of 1 to 8 puffs per day with variation in dosages due to the severity of the condition being treated, the weight of the patient and the particle size distribution of the aerosol since smaller particles will achieve greater lung penetration. Propellants, e.g., a fluorinated hydrocarbon or isobutane, containers, valves and actuators for liquid aerosols are described by L. Lachman et al. in "The Theory and Practice of Industrial Pharmacy", Lea and Febiger, Philadelphia (1976).

In the following Examples and throughout the specification, the following abbreviations are used: atm (atmospheres); bp (boiling point); °C. (degrees Centigrade); g (grams); hr (hours); mg (milligrams); min (minutes); ml (milliliters); mmol (millimoles); mp (melting point); N (normal); nm (nanometers); nM (nanomolar); $R_f$ (relative mobility in TLC); TLC (thin layer chromatography); DCC (dicyclohexylcarbodiimide); DMF (dimethylformamide); DMSO (dimethyl sulfoxide); Et$_2$O (diethyl ether); EtOAc (ethyl acetate); HOAc (acetic acid); HOBT (hydroxybenzotriazole); MeOH (methyl alcohol); Pd/C (palladium on charcoal catalyst); pNA (paranitroanilide); and THF (tetrahydrofuran). In addition, C, H, N, etc. (the conventional symbols for the elements) are used.

The L-configuration is indicated in the following Examples and throughout the specification in all instances where chirality exists and the configuration is not specified.

EXAMPLE 1

N-alpha-t-Butyloxycarbonyl-N-epsilon-benzyloxycarbonyl-L-lysyl-L-valyl-L-prolyl-L-valinal Formula (I): $R^1 = -CH(CH_3)_2$; $R^2 = -CH(CH_3)_2$; $R^3 = -(CH_2)_4NHCOOCH_2C_6H_5$; $R^4 = -OC(CH_3)_3$.

a. N-alpha-t-Butyloxycarbonyl-L-valyl-L-proline methyl ester

1-Hydroxybenzotriazole (65.4 g, 0.484 mol) was added to a solution of N-t-butyloxycarbonyl-L-valine (52.5 g, 0.242 mol) in 600 ml of dry DMF at 0° C. under a nitrogen atmosphere and stirred for 15 min. To the resulting solution was added a suspension of L-proline methyl ester hydrochloride (40.0 g, 0.242 mol) with TEA (36 ml, 0.25 mol) in dry DMF followed by DCC (55.0 g, 0.266 mol). The mixture was stirred for 3 hr. at 0° C. and then at room temperature for 4 days. The reaction mixture was filtered and the filtrate concentrated under vacuum. The resulting residue was mixed with 1.0 l of EtOAc and filtered. The filtrate was washed successively with 20% aqueous citric acid, brine, saturated aqueous NaHCO$_3$ and brine. The organic phase was dried over Na$_2$SO$_4$, filtered and concentrated to give 80.7 g of the product as a thick yellow syrup; TLC, $R_f=0.4$, silica gel, EtOAc:CHCl$_3$ (15:85).

b. L-Valyl-L-proline methyl ester hydrochloride

A solution of 6N HCl/EtOAc (200 ml) was added to a solution of the product of Example 1a in EtOAc (300 ml) at 0° C. The reaction mixture was warmed to room temperature and stirred overnight. The resulting solution was concentrated under vacuum. The residual solid was triturated with Et$_2$O to afford 33.9 g of the product as a white solid.

c. N-alpha-t-Butyloxycarbonyl-N-epsilon-benzyloxycarbonyl-L-lysyl-L-valyl-L-proline methyl ester Isobutyl chloroformate (16.7 g, 0.122 mol) was added to a solution of N-alpha-t-butyloxycarbonyl-N-epsilon-benzyloxycarbonyl-L-lysine (46.4 g, 0.122 mol), N-methylmorpholine (13.2 g, 0.13 mol) in dry THF (300 ml) at −25° C. under a nitrogen atmosphere. A white precipitate immediately formed. The reaction mixture was stirred for 1 hr. and then cooled to −60° C. A pre-cooled (−78° C.) suspension of the product of Example 1b (33.0 g, 0.122 mol) with N-methylmorpholine (13.2 g, 0.13 mol) in dry THF (300 ml) was added in one portion. The reaction mixture was warmed slowly to room temperature and stirred overnight. The resulting mixture was filtered and the filtrate concentrated under vacuum to give a residue which was dissolved in EtOAc and washed successively with aqueous 1N HCl, saturated aqueous $NaHCO_3$ and brine. The organic phase was dried over $Na_2SO_4$, filtered and concentrated under vacuum to give the product (82.0 g) as a pale yellow oil; TLC, $R_f$=0.65, silica gel, EtOAc.

d. N-alpha-t-Butyloxycarbonyl-N-epsilon-benzyloxycarbonyl-L-lysyl-L-valyl-L-proline A solution of NaOH (0.75 g, 18.75 mmol) in $H_2O$ (10 ml) was added to a stirred solution of the product of Example 1c (10.1 g) in MeOH (50 ml) at room temperature. The reaction mixture was stirred overnight and then concentrated under vacuum. The resulting residue was dissolved in $H_2O$ and the solution extracted with $Et_2O$. The aqueous layer was acidified with 5% aqueous citric acid and extracted with EtOAc. The organic phase was dried with $Na_2SO_4$, filtered and concentrated under vacuum to give the product (9.27 g) as a white solid; TLC, $R_f$=0.55, silica gel, MeOH:CHCl$_3$:HOAc (9.5:90:0.5).

e. N-alpha-t-Butyloxycarbonyl-N-epsilon-benzyloxycarbonyl-L-lysyl-L-valyl-L-prolyl-L-valinol A solution of the product of Example 1d in dry THF (100 ml) under a nitrogen atmosphere was cooled to −20° C. N-methylmorpholine (1.6 ml; 14.8 mmol) was added followed by isobutylchloroformate (1.9 ml, 14.8 mmol). The mixture was stirred for 10 min. and then cooled to −40° C. A solution of L-valinol (1.5 g; 14.8 mmol) in dry THF (50 ml) was added dropwise. The solution was allowed to warm slowly to room temperature and stirred overnight. The reaction mixture was filtered, the filtrate concentrated under vacuum and the residue dissolved in EtOAc. The EtOAc solution was washed successively with aqueous 1N HCl, saturated aqueous $NaHCO_3$ and brine. The organic phase was dried with $Na_2SO_4$, filtered and concentrated in vacuum to give 9.06 g of the crude alcohol. The alcohol was purified by flash chromatography on silica gel with MeOH:EtOAc (3:97) as the eluent to give the product; TLC, $R_f$=0.25, silica gel, MeOH:EtOAc (5:95).

Elemental Analysis: Calculated for $C_{34}H_{55}N_5O_8 \cdot H_2O$: C, 60.07; H, 8.45; N, 10.30. Found: C, 60.00; H, 8.22; N, 10.55.

f. N-alpha-t-Butyloxycarbonyl-N-epsilon-benzyloxycarbonyl-L-lysyl-L-valyl-L-prolyl-L-valinal A solution of DMSO (85 microliters) in dry $CH_2Cl_2$ (1ml) was added dropwise with a syringe to a stirred solution of oxalyl chloride (52 microliters, 0.6 mmol) in dry $CH_2Cl_2$ (1 ml) cooled to −23° C. under a nitrogen atmosphere. A solution of the product of Example 1e (0.20 g, 0.3 mmol) in $CH_2Cl_2$ (1.5 ml) was added in the same manner. The reaction mixture was stirred for 30 minutes and TEA (166 microliters, 1.2 mmol) added dropwise with a syringe. The reaction mixture was allowed to slowly warm to room temperature and then diluted with $CH_2Cl_2$ and washed successively with 10% aqueous acetic acid, 5% aqueous $NaHCO_3$ and brine. The organic phase was dried with $Na_2SO_4$, filtered and concentrated under vacuum to give the crude aldehyde. The aldehyde was purified using two successive flash chromatographies with silica gel and eluents of $CH_2Cl_2$:EtOAc (3:7) and MeOH:CHCl$_3$ (3:97) respectively to give the product (90 mg); TLC, $R_f$=0.45, silica gel, MeOH:Et$_2$O (5.95).

Elemental Analysis: Calculated for $C_{34}H_{53}N_5O_8 \cdot H_2O$: C, 60.24; H, 8.18; N, 10.33. Found: C, 60.01; H, 7.84; N, 10.09.

Preparation of bisulfite adducts of this and other Formula (I) aldehydes of this invention is described in Example 31.

EXAMPLE 2

N-alpha-t-Butyloxycarbonyl-N-epsilon-benzyloxycarbonyl-L-lysyl-N-epsilon-benzyloxycarbonyl-L-lysyl-L-prolyl-L-valinal Formula (I): $R^1$=—CH(CH$_3$)$_2$; $R^2$=—(CH$_2$)$_4$NHCOOCH$_2$C$_6$H$_5$; $R^3$=—(CH$_2$)$_4$NHCOOCH$_2$C$_6$H$_5$; $R^4$=—OC(CH$_3$)$_3$.

a. N-alpha-t-Butyloxycarbonyl-N-epsilon-benzyloxycarbonyl-L-lysyl-N-epsilon-benzyloxycarbonyl-L-lysine methyl ester A solution of isobutyl chloroformate (0.79 g, 5.79 mmol) in $CH_2Cl_2$ (10 ml) was added dropwise to a stirred solution of N-alpha-t-butyloxycarbonyl-N-epsilon-benzyloxycarbonyl-L-lysine (2.00 g, 5.26 mmol) and N-methylmorpholine (1.33 g, 13.15 mmol) in $CH_2Cl_2$ (50 ml) cooled to −23° C. under a nitrogen atmosphere. The mixture was stirred for an additional 15 min. and N-epsilon-benzyloxycarbonyl-L-lysine methyl ester hydrochloride (1.74 g, 5.26 mmol) was added. The reaction mixture was allowed to warm slowly to room temperature and stirred overnight. The mixture was washed successively with 5% aqueous $NaHCO_3$, twice with 5% aqueous citric acid, and brine. The organic phase was dried with $Na_2SO_4$, filtered and concentrated under vacuum. The product was purified by flash chromatography on silica gel with MeOH:CHCl$_3$(3:97) as the eluent to give the product (2.20 g) as a clear syrup. The compound was triturated with Et$_2$O to give the product as a white precipitate; mp=108°-110° C.; TLC, $R_f$=0.59, silica gel, MeOH:CHCl$_3$ (3:97).

b. N-alpha-t-Butyloxycarbonyl-N-epsilon-benzyloxycarbonyl-L-lysyl-N-epsilon-benzyloxycarbonyl-L-lysine The product of Example 2a (0.12 g, b 3.05 mmol) was mixed with NaOH (0.12 g, 3.05 mmol) and MeOH (50 ml) and stirred overnight at room temperature. The solution was concentrated under vacuum at room temperature and the resulting residue dissolved in $H_2O$ (40 ml). HOAc (3.36 mmol) was added and the solid product was isolated by decantation. The product was dissolved in $CH_2Cl_2$, washed successively with 5% aqueous citric acid and brine, and dried with $Na_2SO_4$. The solution was filtered and concentrated under vacuum to give the product (1.62 g) as a clear syrup; TLC, $R_f=0.10$, silica gel, MeOH:$CHCl_3$ (5:95).

c. N-alpha-t-Butyloxycarbonyl-N-epsilon-benzyloxycarbonyl-L-lysyl-N-epsilon-benzyloxycarbonyl-L-lysyl-L-proline methyl ester The title compound was prepared as in Example 2a, using the product of Example 2b (1.51 g, 2.35 mmol) and N-methylmorpholine (0.59 g, 5.88 mmol) in $CH_2Cl_2$ (50 ml) and adding isobutyl chloroformate (0.35 g, 2.59 mmol) and L-proline methyl ester hydrochloride (0.39 g, 2.35 mmol) to give the product (0.95 g); TLC, $R_f=0.95$, silica gel, MeOH:$CHCl_3$ (3:97).

d. N-alpha-t-Butyloxycarbonyl-N-epsilon-benzyloxycarbonyl-L-lysyl-N-epsilon-benzyloxycarbonyl-L-lysyl-L-proline The title compound was prepared as in Example 2b using the product of Example 2c (0.95 g, 1.26 mmol), NaOH (0.56 g, 1.4 mmol) and MeOH (50 ml). The product was purified by flash chromatography on silica gel with MeOH:$CHCl_3$:HOAc (4.5:95:0.5) to give the product (0.75 g); TLC, $R_f=0.50$, silica gel, MeOH:$CHCl_3$:HOAc (4.5:95:0.5).

e. N-alpha-t-Butyloxycarbonyl-N-epsilon-benzyloxycarbonyl-L-lysyl-N-epsilon-benzyloxycarbonyl-L-lysyl-L-prolyl-L-valinol The title compound was prepared as in Example 2a using the product of Example 2d (0.42 g, 0.568 mmol) and N-methylmorpholine (0.06 g, 0.568 mmol) in $CH_2Cl_2$ (25 ml) and adding isobutyl chloroformate (0.08 g, 0.568 mmol) and L-valinol (0.06 g, 0.568 mmol). The product was purified by flash chromatography on silica gel using MeOH:$CHCl_3$ (3.97) as eluent to give the title compound (0.18 g); TLC, $R_f=0.48$, silica gel, MeOH:$CHCl_3$ (3:97).

f. N-alpha-t-Butyloxycarbonyl-N-epsilon-benzyloxycarbonyl-L-lysyl-N-epsilon-benzyloxycarbonyl-L-lysyl-L-prolyl-L-valinal The title compound was prepared as in Example 1f using oxalyl chloride (0.03 g, 0.213 mmol) in $CH_2Cl_2$ (2 ml) and adding DMSO (0.03 g, 0.380 mmol) in $CH_2Cl_2$ (2 ml), the product of Example 2e (0.16 g, 0.194 mmol) in $CH_2Cl_2$ (2 ml), and TEA (0.10 g, 1 mmol) in $CH_2Cl_2$ (2 ml). The crude mixture was separated by flash chromatography to give the product (0.022 g); TLC, $R_f=0.47$, silica gel, MeOH:$CHCl_3$ (3:97).

Elemental Analysis: Calculated for $C_{43}H_{62}N_6O_{10}$: C, 62.75; H, 7.59; N, 10.21. Found: C, 62.54; H, 7.45; N, 10.41.

EXAMPLE 3

N-alpha-t-Butyloxycarbonyl-N-epsilon-picolinyl-L-lysyl-L-valyl-L-prolyl-L-valinal Formula (I): $R^1 = -CH(CH_3)_2$; $R^2 = -CH(CH_3)_2$; $R^3 = -(CH_2)_4NHCO$-2-pyridyl; $R^4 = -OC(CH_3)_3$.

a. N-alpha-t-Butyloxycarbonyl-L-lysyl-L-valyl-L-proline methyl ester

The product of Example 1c (5.88 g, 9.95 mmol) was mixed with 10% Pd/C (1.25 g) and MeOH (100 ml) and placed in a Parr shaker (3 atm. of $H_2$). The reaction was stopped after the theoretical amount of $H_2$ was consumed. The mixture was filtered through diatomaceous earth (Celite®) and concentrated under vacuum to give the product (4.46 g); TLC, $R_f=0.10$, silica gel, MeOH:$CHCl_3$ (3:97). (Celite® is a registered trademark of Manville Corporation, Denver, Colo., U.S.A.).

b. N-alpha-t-Butyloxycarbonyl-N-epsilon-picolinyl-L-lysyl-L-valyl-L-proline methyl ester A solution of picolinic acid (0.65 g, 5.32 mmol), HOBT (1.44 g, 10.64 mmol) and N-methylmorpholine (0.54 g, 5.32 mmol) in DMF (100 ml) was cooled to 0° C. and DCC (1.21 g, 5.85 mmol) added. The mixture was stirred for an additional 15 min. and the product of Example 3a (2.43 g, 5.32 mmol) added. The reaction mixture was allowed to warm to room temperature and stirred overnight. The mixture was filtered and concentrated under vacuum. The residue was dissolved in $CH_2Cl_2$, washed successively with $H_2O$, three times with 5% aqueous $NaHCO_3$ and brine. The organic layer was dried over $Na_2SO_4$, filtered and concentrated under vacuum to give the crude product, which was purified by flash chromatography on silica gel with MeOH:$CHCl_3$ (5:95) as eluent to give the product (1.45 g) as a tan hygroscopic foam; TLC, $R_f=0.35$, silica gel, MeOH:$CHCl_3$ (5:95).

c. N-alpha-t-Butyloxycarbonyl-N-epsilon-picolinyl-L-lysyl-L-valyl-L-proline

The title compound was prepared as in Example 2b, using the product of Example 3b (1.05 g, 1.87 mmol) and NaOH (0.11 g, b 2.8 mmol) in MeOH (50 ml) to give the product (0.87 g); TLC, $R_f=0.80$, silica gel, MeOH:$CHCl_3$ (5:95).

d. N-alpha-t-Butyloxycarbonyl-N-epsilon-picolinyl-L-lysyl-L-valyl-L-prolyl-L-valinol The title compound was prepared as in Example 2a using the product of Example 3c (1.17 g, 2.14 mmol) and N-methylmorpholine (0.24 g, 2.35 mmol) in $CH_2Cl_2$ (40 ml) and adding isobutyl chloroformate (0.29 g, 2.14 mmol) in $CH_2Cl_2$ (20 ml) followed by L-valinol (0.22 g, 2.14 mmol) to give the product (1.07 g) as a white foam; TLC, $R_f=0.35$, silica gel, MeOH:$CHCl_3$ (3:97).

e. N-alpha-t-Butyloxycarbonyl-N-epsilon-picolinyl-L-lysyl-L-valyl-L-prolyl-L-valinal The title compound was prepared as in Example 1f using oxalyl chloride (0.92 g, 7.25 mmol) in $CH_2Cl_2$ (20 ml) and adding DMSO (1.13 g, 14.5 mmol) in $CH_2Cl_2$ (5 ml), the product of Example 3d (0.92 g, 1.45 mmol) in $CH_2Cl_2$ (5 ml), and TEA (7.34 g, 72.5 mmol) in $CH_2Cl_2$ (5 ml). The crude mixture was purified by flash chromatography on silica gel with $MeOH:CHCl_3$ (5:95) to give the product (0.23 g); TLC, $R_f=0.66$, silica gel, $MeOH:CHCl_3$, (5:95).

Elemental Analysis: Calculated for $C_{32}H_{50}N_6O_7.2-H_2O$: C, 57.64; H, 8.16; N, 12.61. Found: C, 57.57; H, 7.96; N, 12.51.

EXAMPLE 4

N-alpha-t-Butyloxycarbonyl-N-epsilon-phenylcarbamoyl-L-lysyl-L-valyl-L-proplyl-L-valinal Formula (I): $R^1 = -CH(CH_3)_2$; $R^2 = -CH(CH_3)_2$; $R^3 = -(CH_2)_4NHCONHC_6H_5$; $R^4 = -OC(CH_3)_3$.

a. N-alpha-t-Butyloxycarbonyl-N-epsilon-phenylcarbamoyl-L-lysyl-L-valyl-L-proline methyl ester A solution of the product of Example 3a (1.0 g, 2.0 mmol) and phenyl isocyanate (0.23 ml, 2.1 mmol) in $CHCl_3$ (15 ml) was stirred at room temperature for 24 hrs. The reaction mixture was concentrated under vacuum, the residue dissolved in EtOAc, and the solution washed successively with aqueous 1N HCl, saturated aqueous $NaHCO_3$ and brine. The organic layer was dried over $Na_2SO_4$, filtered and concentrated under vacuum to give the product (1.25 g), as a white foam; TLC, $R_f=0.36$, silica gel, EtOAc.

b. N-alpha-t-Butyloxycarbonyl-N-epsilon-phenylcarbamoyl-L-lysyl-L-valyl-L-proline The title compound was prepared as in Example 1d, using the product of Example 4a (0.75 g, 1.25 mmol), 1N NaOH (1.4 ml, 1.4 mmol) and MeOH (5 ml) to give the product (0.76 g).

c. N-alpha-t-Butyloxycarbonyl-N-epsilon-phenylcarbamoyl-L-lysyl-L-valyl-L-prolyl-L-valinol A solution of the product of Example 4b (0.76 g, 1.3 mmol) in dry THF (10 ml) was cooled to $-20°$ C. under a nitrogen atmosphere. N-methylmorpholine (0.15 ml, 1.3 mmol) was added followed by isobutyl chloroformate (0.17 ml, 1.3 mmol). The reaction mixture was stirred for 10 min. and the temperature lowered to $-45°$ C. A solution of L-valinol (0.135 g, 1.3 mmol) in dry THF (5 ml) was added. The reaction mixture was allowed to warm to room temperature and stirred overnight. The reaction mixture was filtered, concentrated under vacuum, and the residue purified by flash chromatography on silica gel with MeOH:EtOAc (10:90) to give the product (0.68 g); TLC, $R_f=0.41$, silica gel, MeOH:EtOAc (1:9).

d. N-alpha-t-Butyloxycarbonyl-N-epsilon-phenylcarbamoyl-L-lysyl-L-valyl-L-prolyl-L-valinal The title compound was prepared as in Example 1f, using oxalyl chloride (0.12 ml, 1.78 mmol) in $CH_2Cl_2$ (0.5 ml) and adding DMSO (0.32 ml, 3.56 mmol) in $CH_2Cl_2$ (0.5 ml), the product of Example 4c (0.6 g, 0.89 mmol) in $CH_2Cl_2$ (1 ml) and TEA (0.49 ml, 3.56 mmol). The crude product was purified by flash chromatography on silica gel with $MeOH:Et_2O$ (10:90) to give the product (0.41 g) as a white foam; TLC, $R_f=0.43$, silica gel, $MeOH:Et_2O$ (1:9).

EXAMPLE 5

N-alpha-Succinyl-N-epsilon-benzyloxycarbonyl-L-lysyl-L-valyl-L-prolyl-L-valinal

Formula (I): $R^1 = -CH(CH_3)_2$; $R^2 = -CH(CH_3)_2$; $R^3 = -(CH_2)_4NHCOOCH_2-C_6H_5$; $R^4 = -CH_2CH_2COOH$.

a. N-alpha-Succinyl-N-epsilon-benzyloxycarbonyl-L-lysyl-L-valyl-L-prolyl-L-valinol A solution of the product of Example 1e (3.57 g, 5.4 mmol) and trifluoroacetic acid (4.2 ml, 54 mmol) in $CH_2Cl_2$ (10 ml) was stirred at room temperature for 2 hr. The reaction mixture was concentrated under vacuum, the residue was dissolved in $CH_3CN$ (90 ml), and N-methylmorpholine (6.0 ml, 54 mmol) was added. The reaction mixture was cooled to 0° C. and a solution of succinic anhydride (0.59 g, 5.9 mmol) in $CH_3CN$ (10 ml) was added dropwise. The reaction mixture was kept at 5° C. for 72 hr. and then concentrated under vacuum. The residue was dissolved in EtOAc, washed successively with aqueous 1N HCl and brine, dried over $Na_2SO_4$ and filtered. The EtOAc solution was concentrated under vacuum to give the product as a viscous yellow oil; TLC, $R_f=0.4$, silica gel, $MeOH:CHCl_3$ (1:9). The yellow oil obtained, will, on standing, slowly convert to an unidentified secondary product (TLC, $R_f=0.6$, silica gel, $MeOH:CHCl_3$ (1:9)) which can be re-converted to the desired product by treatment with aqueous MeOH containing 1.1 equivalents of NaOH.

b. N-alpha-Succinyl-N-epsilon-benzyloxycarbonyl-L-lysyl-L-valyl-L-prolyl-L-valinal The title compound was prepared as described in Example 1 f using oxalyl chloride (0.175 ml, 2.0 mmol) in dry $CH_2Cl_2$ (1 ml) and adding DMSO (0.28 ml, 4.0 mmol) in $CH_2Cl_2$ (0.5 ml), the product of Example 5a (0.7 g, 1.06 mmol) in $CH_2Cl_2$ (2ml) and TEA (0.55 ml, 4.0 mmol) to give the crude product (0.660 g) as a pale yellow foam. Purification by flash chromatography on silica gel (Baker, acidic) using an eluent of $MeOH:CHCl_3$ (5:95) gave the product (0.188 g); TLC, $R_f=0.45$, silica gel, $MeOH:CHCl_3:HOAc$ (9.5:90:0.5).

Elemental Analysis: Calculated for $C_{33}H_{49}N_5O_9.\frac{1}{2}H_2O$: C, 59.26; H, 7.53; N, 10.47. Found: C, 59.48; H, 7.27; N, 10.31.

$^1H$-NMR (dimethyl sulfoxide-$d_6$): delta 9.45 (1H, s), 8.16 (1H, d), 7.98 (1H, d), 7.82 (1H, d), 7.34 (5H, m), 7.22 (1H, dd), 5.0 (2H, s), 4.44 (1H, m), 4.26 (2H, m), 4.07 (1H, m), 3.74 (1H, m), 3.56 (1H, m), 2.96 (2H, m), 2.4 (4H, m), 2.26-1.16 (12H, m), 0.86 (12H, m).

EXAMPLE 6

N-alpha-Succinyl-N-epsilon-benzyloxycarbonyl-L-lysyl-L-valyl-L-prolyl-L-valinal-Alternate Synthesis Formula (I): $R^1 = -CH(CH_3)_2$; $R^2 = -CH(CH_3)_2$; $R^3 = -(CH_2)_4NHCOOCH_2-C_6H_5$; $R^4 = -(CH_2)_2CO_2H$ a. N-Benzyloxycarbonyl-L-valyl-L-proline t-butyl ester

A solution of N-benzyloxycarbonyl-L-valine (56.25 g, 0.244 mol) and HOBT (60.67 g, 0.45 mol) in DMF (565 ml) was cooled to 5° C. DCC (50.89 g, 0.247 mol) was added in one portion. The mixture was stirred an additional 15 min. at 5° C. and then L-proline t-butyl ester (38.36 g, 0.224 mol) was added. The mixture was stirred an additional 2 hr. at 5° C. then for 48 hr. at room temperature. The mixture was filtered and concentrated under vacuum. The oily residue was dissolved in EtOAc (1 liter) and washed successively with 20% aqueous citric acid, saturated aqueous NaHCO₃ and brine. The organic phase was dried over Na₂SO₄, filtered and concentrated under vacuum to afford the product (92 g) as a white foam; TLC, $R_f = 0.9$ silica gel, CHCl₃/EtOAc (85:15).

b. L-Valyl-L-proline t-butyl ester

A mixture of the product of Example 6a (92 g. 0.227 mol) and 10% Pd/C (10 g) in EtOH (1 liter) was hydrogenated on a Parr shaker for 6 hr. at 60 psi at room temperature. The mixture was filtered through Celite ® and concentrated under vacuum to afford the product (62 g) as a viscous yellow oil; TLC, $R_f = 0.3$, silica gel, MeOH/CHCl₃ (10:90).

c. N-alpha-t-Butyloxycarbonyl-N-epsilon-benzyloxycarbonyl-L-lysyl-L-valyl-L-proline t-butyl ester HOBT (8.55 g, 0.06 mol) and DCC (7.35 g, 0.036 mol) were added to a solution of N-alpha-t-butyloxycarbonyl-N-epsilon-benzyloxycarbonyl-L-lysine (12.0 g, 0.03 mol) in dry THF (200 ml) at 5° C. The mixture was stirred for 15 min. at 5° C. To the mixture was then added the product of Example 6b (9.16 g, 0.03 mol). The resulting solution was allowed to warm slowly to room temperature and was stirred for 24 hr. The mixture was filtered and concentrated under vacuum. The oily residue was dissolved in EtOAc (500 ml) and washed successively with 20% aqueous citric acid, saturated aqueous NaHCO₃ and brine. The organic phase was dried over Na₂SO₄, filtered and concentrated under vacuum to give the product (20 g) as a yellow foam; TLC, $R_f = 0.6$, silica gel, CHCl₃:MeOH (95:5).

d. N-epsilon-Benzyloxycarbonyl-L-lysyl-L-valyl-L-proline trifluoroacetate salt Trifluoroacetic acid (25 ml, 0.32 mol) was added to a solution of the product of Example 6c (10.38 g, 16.4 mmol) in CH₂Cl₂ (25 ml) at room temperature and the resulting mixture was stirred for 5 hr. The solution was concentrated under vacuum and the residue triturated with Et₂O. The product was isolated by filtration and dried under vacuum to give a white solid (7.4 g).

e. N-alpha-(3-Carbomethoxypropionyl)-N-epsilon-benzyloxycarbonyl-L-lysyl-L-valyl-L-proline Aqueous 1N NaOH (460 ml, 0.46 mol) was added dropwise to a solution of the product of Example 6d (136.5 g, 0.23 mol) in CH₂Cl₂ (1.5 liters) at room temperature. The mixture was cooled to 0° C. and 3-carbomethoxypropionyl chloride (34.6 g, 0.23 mol) was added dropwise. The resulting solution was stirred vigorously for 12 min. The solution was removed from the ice bath, diluted with H₂O (800 ml), and adjusted to pH 2.0 by dropwise addition of aqueous 1N HCl (40 ml). The organic phase was separated and the aqueous layer was extracted with CH₂Cl₂ (2×500 ml). The organic layers were combined, washed successively with H₂O (2×500 ml) and brine (500 ml), dried over Na₂SO₄ and filtered. The filtrate was concentrated under vacuum to give the crude product (126.4 g); TLC, $R_f = 0.25$, silica gel, MeOH/CHCl₃/HOAC (5:94.5:0.5).

f. N-Benzyloxycarbonyl-L-valinol

Benzyl chloroformate (91.0 g, 0.532 mol, 95% purity) was added dropwise over a period of 1 hr. to a precooled (0° C.) solution of L-valinol (50.0 g, 0.484 mol) and triethylamine (60.0 g, 0.6 mol) in CHCl₃ (1500 ml). The reaction mixture was stirred for 1 hr. at 0° C. and then allowed to warm to room temperature over 2 hr. The reaction mixture was concentrated under vacuum. EtOAc (1500 ml) was added to the resulting residue and the organic solution was washed with aqueous 1N NaOH and brine. The organic phase was dried over MgSO₄, filtered and concentrated under vacuum. The resulting residue was purified by flash chromatography on a column of silica gel (6 cm × 30 cm) using a stepwise gradient of Et₂O:hexane (1:5) followed by pure Et₂O to give the product (91.4 g) as a white waxy solid; TLC, $R_f = 0.23$, silica gel, hexane:Et₂O (50:50).

g. N-Benzyloxycarbonyl-L-valinal

A solution of DMSO (107.2 g, 1.372 mol) in CH₂Cl₂ (150 ml) was added dropwise over 0.5 hr. to a precooled (−60° C.), stirred solution of oxyalyl chloride (87.1 g, 0.686 mol) in CH₂Cl₂ (800 mls) under a nitrogen atmosphere. The temperature of the mixture rose to −45° C. The reaction mixture was then warmed to −30° C. A solution of the product of Example 6f (81.5 g, 0.343 mol) in CH₂Cl₂ (300 ml) was added dropwise over 45 min. at −30° C. The reaction mixture was stirred for 50 min. at −25° C., cooled to −40° C. and a solution of diisopropylethyl amine (177.4 g, 1.372 mol) in CH₂Cl₂ (250 ml) was added dropwise over 45 min. at −40° C. The reaction mixture was stirred for 1 hr. as it warmed to room temperature. The reaction mixture was diluted with CH₂Cl₂ (1500 ml) and the organic phase was washed with aqueous 1N HCl and then concentrated under vacuum to give the product (98 g) as a green oil which was used immediately without further purification; TLC, $R_f = 0.48$, silica gel, hexane:Et₂O (50:50).

h. N-Benzyloxycarbonyl-L-valinal diethylacetal

Triethyl orthoformate (700 g, 4.723 mol), absolute EtOH (800 ml) and p-toluenesulfonic acid monohydrate (5.0 g, 0.026 mol) were added to the product of Example 6g (81 g, 0.343 mol). The mixture was stirred for 10 minutes at room temperature and then concentrated under vacuum. The resulting residue was dissolved in Et₂O and washed with saturated aqueous NaHCO₃. The organic phase was dried over Na₂SO₄, filtered and concentrated under vacuum to give the crude product. This product was purified by flash chromatography with silica gel using a stepwise gradient of hexane through mixtures of CH₂Cl₂:hexane to EtOAc:CH₂Cl₂ (30:70) to give the product as a pale yellow oil; TLC, $R_f$=0.21, silica gel, CH₂Cl₂:petroleum ether (50:50).

i. L-Valinal diethylacetal

A mixture of the product of Example 6h (147.8 g, 0.478 mol) and 10% Pd/C (10 g) in EtOAc (1500 ml) was stirred under H₂ (1 atm.) until 2500 ml of H₂ was consumed. Twice during this time the reaction was interrupted and 10% Pd/C (10 g) was added. The reaction mixture was then filtered through a pad of Celite ®. 10% Pd/C (10 g) was added and the reaction mixture stirred until 10.92 liters of H₂ was consumed. The reaction mixture was filtered through Celite ® and the filtrate was concentrated under vacuum to give the product (78.8 g) as a pale yellow oil; [alpha]$_D^{25}$+7.8.

j. N-alpha-(3-Carbomethoxypropionyl)-N-epsilon-benzyloxycarbonyl-L-lysyl-L-valyl-L-prolyl-L-valinal diethylacetal Isobutyl chloroformate (27.32 g, 0.20 mol) was added to a solution of the product of Example 6e (118 g, 0.20 mol) and N-methylmorpholine (20.23 g, 0.20 mol) in dry THF (1500 ml) at −15° C. The reaction mixtures was stirred for 0.5 hr. at −15° C. and then cooled to −40° C. A solution of the product of Example 6i (35.05 g, 0.20 mol) in dry THF (250 ml) was added dropwise. The resulting mixture was allowed to warm slowly to room temperature and stirred overnight. The reaction mixture was filtered and the filtrate was concentrated under vacuum. The residue was partially purified by flash chromatography on silica gel with a stepwise gradient from pure Et₂O to MeOH:Et₂O (10:90). Final purification on a Waters Prep 500 ® Liquid Chromatograph equipped with silica gel columns using MeOH:Et₂O:CH₂Cl₂ (2.5:40:60) as eluent gave the product (87.5 g, 58%).

k. N-alpha-Succinyl-N-epsilon-benzyloxycarbonyl-L-lysyl-L-valyl-L-prolyl-L-valinal A solution of aqueous 1N NaOH (14 ml, 14 mmol) was added to a solution of the product of Example 6j (10.0 g, 13.4 mmol) in MeOH/H₂O (1:1, 280 ml) at room temperature. The mixture was stirred for 2–4 hrs. The MeOH was removed under vacuum to give an aqueous solution.

Dowex ®50WX8-H resin (500 g), H₂O (1000 ml) and acetone (120 ml) were added to this aqueous solution. This mixture was stirred at room temperature for 24 hr. The mixture was filtered and the resin was washed with acetone (1.0 liter). The filtrate and the washings were combined and the acetone was removed under vacuum. The H₂O was removed using a lyophilizer to give the product (7.8 g, 11.8 mmol) as a white, fluffy solid; TLC, $R_f$=0.3, silica gel, MeOH:CHCl₃:HOAc (5:95:0.5).

l. Sodium salt of N-alpha-succinyl-N-epsilon-benzyloxycarbonyl-L-lysyl-L-valyl-L-prolyl-L-valinal A solution of the product of Example 6k (100 mg, 0.150 mmol) in water (100 ml) was treated with aqueous 1N NaOH (0.15 ml) and then stirred for 10 min. at room temperature. The water was removed with a lyophilizer to give the sodium salt as a white powder.

¹H-NMR (dimethyl sulfoxide-d₆): delta 9.43 (1H, s), 8.57 (1H, d, J=7.5 Hz), 8.20 (1H, d, J=7.6 Hz), 8.03 (1H, d, J=7.6 Hz), 7.34 (6H, m), 4.99 (2H, s), 4.44 (1H, m), 4.29 (1H, m), 4.13 (1H, m), 4.02 (1H, m), 3.68 (1H, m), 3.51 (1H, m), 2.95 (2H, m), 2.36–1.16 (16H, m), 0.86 (12H, m).

Other acids of the invention may also be converted to their corresponding sodium salts by this procedure.

m. Dilysine adduct of N-alpha-succinyl-N-epsilon-benzyloxycarbonyl-L-lysyl-L-valyl-L-prolyl-L-valinal L-Lysine (113 mg, 0.778 mmol) was added to a solution of the product of Example 6k (250 mg, 0.389 mmol) in MeOH:H₂O (1:1, 10 ml). The mixture was stirred at room temperature for 10 min. The methanol was removed under vacuum and the aqueous solution was lyophilized to give the product (370 mg) as a white solid.

Elemental Analysis: Calculated for C₄₅H₇₆N₉O₁₃.2-H₂O: C, 54.75; H, 8.16; N, 12.77. Found: C, 54.64; H, 8.08; N, 12.58.

Adducts of other compounds of the invention may be prepared in a similar manner. If a carboxylic acid group is not present in the molecule, only one equivalent of the amine is used.

This Example 6 illustrates the preferred method for preparing the title compound.

EXAMPLE 7

N-alpha-Succinyl-N-epsilon-benzyloxycarbonyl-L-lysyl-L-valyl-L-prolyl-D-valinal

Formula I: $R^1$=(D)-CH(CH₃)₂; $R^2$=—CH(CH₃)₂; $R^3$=—(CH₂)₄—NHCOOCH₂C₆H₅; $R^4$=—(CH₂)₂COOH a. N-alpha-Succinyl-N-epsilon-benzyloxycarbonyl-L-lysyl-L-valyl-L-prolyl-D-valinal diethylacetal HOBT (1.85 g, 13.68 mmol) was added to a solution of the product of Example 6e (4.04 g, 6.84 mmol) and D-valinal diethylacetal (1.2 g, 6.85 mmol) in dry THF (70 ml) at 0° C. under a nitrogen atmosphere and the mixture was stirred for 15 min. To the resulting solution was added 1-(3-dimethylaminopropyl)-3-ethylcarbodiimide hydrochloride (1.44 g, 7.52 mmol) followed by N-methylmorpholine (1.03 g, 10.26 mmol). The mixture was stirred for one hr. at 0° C. and then for 48 hr. at room temperature. The reaction mixture was concentrated in vacuo and the resulting residue was distributed between EtOAc and H₂O. The organic layer was isolated and washed successively with aqueous 1N HCl, brine, saturated aqueous NaHCO₃ and brine, dried over MgSO₄, filtered and concentrated to give a yellow oil. This oil was purified by flash chromatography on silica gel with CH₂Cl₂:Et₂O:MeOH (60:40:3) to give a white foam (2.3 g); TLC, $R_f$=0.4 silica gel, CH₂Cl₂:Et₂O:MeOH (60:40:3).

b. N-alpha-Succinyl-N-epsilon-benzyloxycarbonyl-L-lysyl-L-valyl-L-prolyl-D-valinal 1N NaOH (3.31 ml) was added to a solution of the product of Example 7a (2.3 g, 3.01 mmol) in MeOH:-

$H_2O$ (1:1, 40 ml) at room temperature under a nitrogen atmosphere and the mixture was stirred for 2.5 hr. The MeOH was removed in vacuo and the resulting aqueous solution was diluted with additional $H_2O$ (160 ml) and acetone (20 ml), treated with Dowex ®50 WX8-H resin (120 ml) and stirred for 24 hr. The mixture was filtered and the resin was washed with acetone. The combined filtrates were concentrated to remove the acetone and the $H_2O$ was lyophilized to give a fluffy white solid (1.3 g); TLC, $R_f=0.7$, reverse-phase $C_{18}$ (i.e., octadecylsilane), $MeOH:H_2O$ (75:25).

Elemental Analysis: Calculated for $C_{33}H_{49}N_5O_9 \cdot 0.25H_2O$: C, 59.66; H, 7.51; N, 10.54. Found: C, 59.51; H, 7.24; N, 10.54.

EXAMPLE 8

N-alpha-Methoxysuccinyl-N-epsilon-benzyloxycarbonyl-L-lysyl-L-valyl-L-prolyl-L-valinal Formula (I): $R^1 = —CH(CH_3)_2$; $R^2 = —CH(CH_3)_2$; $R^3 = —(CH_2)_4—NH-COOCH_2C_6H_5$; $R^4 = —(CH_2)_2-COOCH_3$ a. N-alpha-Methoxysuccinyl-N-epsilon-benzyloxycarbonyl-L-lysyl-L-valyl-L-proplyl-L-valinol A solution of the product of Example 1e (3.2 g, 4.84 mmol) and trifluoroacetic acid (3.7 ml, 48 mmol) in $CH_2Cl_2$ (4 ml) was stirred at room temperature for 24 hr. The reaction mixture was concentrated under vacuum, the residue dissolved in THF (60 ml) and cooled to 0° C. under an atmosphere of dry $N_2$. N-methylmorpholine (8.2 ml, 75 mmol) was added, then a solution of 3-carbomethoxypropionyl chloride (0.620 ml, 5.0 mmol) in 10 ml THF was added dropwise. The reaction mixture was stirred at 0° C. for 1 hr., then filtered and concentrated under vacuum. The residue was dissolved in EtOAc, washed successively with $H_2O$, aqueous 1N HCl, saturated aqueous $NaHCO_3$ and brine, dried over anhydrous $Na_2SO_4$ and filtered. The filtrate was concentrated under vacuum to give 3.1 g of an off-white foam. Purification by flash chromatography on silica gel with MeOH:EtOAc (5:95–10:90) gave the desired product (0.95 g); TLC, $R_f=0.35$, silica gel, MeOH:EtOAc (1:9).

b. N-alpha-Methoxysuccinyl-N-epsilon-benzyloxycarbonyl-L-lysyl-L-valyl-L-prolyl-L-valinal The title compound was prepared as described in Example 1f using oxalyl chloride (0.22 ml, 2.54 mmol) in dry $CH_2Cl_2$ (5 ml) and adding DMSO (0.36 ml, 5.08 mmol) in dry $CH_2Cl_2$ (2 ml), the product of Example 8a (0.86 g, 1.27 mmol) in dry $CH_2Cl_2$ (3 ml) and TEA (0.7 ml, 5.08 mmol) to give the crude product as a pale yellow foam. Purification by flash chromatography on silica gel with MeOH:EtOAc (5:95) gave the product (0.75 g); TLC, $R_f=0.58$, silica gel, $MeOH:CHCl_3$ (1:9).

EXAMPLE 9

N-alpha-(4-Carboxybutyryl)-N-epsilon-benzyloxycarbonyl-L-lysyl-L-valyl-L-prolyl-L-valinal Formula (I): $R^1 = —CH(CH_3)_2$; $R^2 = —CH(CH_3)_2$; $R^3 = —(CH_2)_4NH-CO_2CH_2C_6H_5$; $R^4 = —(CH_2)_3CO_2H$.

a. N-alpha-(4-Carbomethoxybutyryl)-N-epsilon-benzyloxycarbonyl-L-lysyl-L-valyl-L-proline Aqueous 1N NaOH (11.86 ml) was added dropwise to a stirred solution of the product of Example 6d (3.5 g, 5.93 mmol) in $CH_2Cl_2$ (70 ml) at room temperature. The mixture was cooled to 0° C. and 4-carbomethoxybutyryl chloride (0.82 ml, 5.93 mmol) was added dropwise. The resulting mixture was stirred vigorously for 12 min. The solution was diluted with $H_2O$ (30 ml), and adjusted to pH 2.0 by dropwise addition of aqueous 1N HCl. The organic layer was collected and the aqueous layer was extracted twice with $CH_2Cl_2$. The combined organic layers were washed successively with $H_2O$ and brine, dried over $Na_2SO_4$, filtered and concentrated under vacuum to give the product (3.23 g); TLC, $R_6=0.25$, silica gel, $MeOH:CHCl_3:HOAC$ (0.45:9.5:0.1).

b. N-alpha-(4-Carbomethoxybutyryl)-N-epsilon-benzyloxycarbonyl-L-lysyl-L-valyl-L-prolyl-L-valinal diethylacetal Isobutyl chloroformate (0.702 ml, 5.42 mmol) was added to a solution of the product of Example 9a (3.2 g, 5.42 mmol) and N-methylmorpholine (0.595 mmol) in dry THF (50 ml) at $-15°$ C. The reaction mixture was stirred for 0.5 hr. at $-15°$ C. and then cooled to $-40°$ C. A solution of L-valinal diethylacetal (0.948 g, 5.42 mmol) in dry THF (7 ml) was added dropwise. The resulting mixture was allowed to warm slowly to room temperature and was stirred overnight. The solution was filtered, the filtrate was concentrated under vacuum, and the product was purified by flash chromatography on silica gel with $Et_2O:CH_2Cl_2:MeOH$ (4:6:3) to give a foam (1.5 g).

Elemental Analysis: Calculated for $C_{39}H_{63}N_5O_{10} \cdot 0.5 H_2O$: C, 60.76; H, 8.36; N, 9.08. Found: C, 60.92; H, 8.25; N, 9.04.

c. N-alpha-(4-Carboxybutyryl)-N-epsilon-benzyloxycarbonyl-L-lysyl-L-valyl-L-prolyl-L-valinal A mixture of the product of Example 9b (0.75 g, 0.985 mmol) in $CH_3OH:H_2O$ (1:1, 20 ml) and aqueous 1N NaOH (1.1 ml) was stirred at room temperature for 4 hr. The methanol was removed under vacuum to give an aqueous solution of the product. Dowex ®50WX8-H resin (38 ml), $H_2O$ (100 ml), acetone (25 ml) were added and the resulting mixture was stirred at room temperature for 48 hr. The mixture was filtered and the resin was washed with acetone (100 ml). The filtrate were combined and concentrated under vacuum to give an aqueous solution which was lyophilized to give the crude product. The product was purified on a reverse-phase column ($C_{18}$) with $MeOH:H_2O$ (60:40) to give a white solid (0.4 g); TLC, $R_f=0.5$, silica gel, $MeOH:CHCl_3:HOAc$ (0.45, 9.5, 0.1).

EXAMPLE 10

N-alpha-N-epsilon-Bis-benzyloxycarbonyl-L-lysyl-L-valyl-L-prolyl-L-valinal

Formula (I): $R^1 = —CH(CH_3)_2$; $R^2 = —CH(CH_3)_2$; $R^3 = —(CH_2)_4-NHCOOCH_2C_6H_5$; $R^4 = —OCH_2C_6H_5$.

a. N-alpha-N-epsilon-Bis-benzyloxycarbonyl-L-lysyl-L-valyl-L-proline t-butyl ester HOBT (5.0 g, 0.037 mol) was added to a solution of N-alpha-N-epsilon-bis-benzyloxycarbonyl-L-lysine (7.66 g, 0.0185 mol) and the product of Example 6b (5.0 g, 0.0185 mol) in 75 ml dry THF at 0° C. under a nitrogen atmosphere. This mixture was stirred for 15 min. and DCC (4.19 g, 0.0203 mol) was then added. The mixture was stirred for 30 min. at 0° C. and then at room temperature for 3 days. The reaction mixture was filtered and the filtrate was concentrated under vacuum. The resulting residue was partitioned between EtOAc (200 ml) and 20% aqueous citric acid (75 ml). The organic layer was isolated and washed with 20% aqueous citric acid (2×75 ml), brine, saturated aqueous NaHCO$_3$ and brine, dried over MgSO$_4$, filtered and concentrated. The residue was purified by flash chromatography on silica gel with CH$_2$Cl$_2$:THF:HOAc (90:10:1) to give a white foam (8.93 g); TLC, R$_f$=0.60 silica gel, CH$_2$Cl$_2$:MeOH (95:5).

b. N-alpha-N-epsilon-Bis-benzyloxycarbonyl-L-lysyl-L-valyl-L-proline

Trifluoroacetic acid (15 ml) was added to a solution of the product of Example 10a (8.93 g) in CH$_2$Cl$_2$ (50 ml) at room temperature under a nitrogen atmosphere. The reaction mixture was stirred for 4 hr., then diluted with toluene (200 ml) and concentrated in vacuo to give a foam (5.73 g).

c. N-alpha-N-epsilon-Bis-benzyloxycarbonyl-L-lysl-L-valyl-L-prolyl-L-valinal diethylacetal HOBT (1.29 g, 9.56 mmol) was added to a solution of the product of Example 10b (3.0 g, 4.78 mmol) and L-valinal diethylacetal (0.84 g, 4.78 mmol) in dry THF (65 ml) at 0° C. under a nitrogen atmosphere. After this mixture was stirred for 15 min, 1-(3-dimethylaminopropyl)-3-ethylcarbodiimide hydrochloride (1.0 g, 5.26 mmol) and N-methylmorpholine (0.72 g, 7.17 mmol) were added. The mixture was stirred for one hour at 0° C. and then at room temperature for 20 hr. The reaction mixture was concentrated in vacuo and the resulting residue was partitioned between EtOAc (100 ml) and H$_2$O (50 ml). The isolated organic layer was washed with 20% aqueous citric acid, brine, saturated aqueous NaHCO$_3$ and brine, then dried over MgSO$_4$, filtered and concentrated. The product was purified by flash chromatography on silica gel with CH$_2$Cl$_2$:Et$_2$O:MeOH (60:40:2) to give a white foam (2.2 g); TLC R$_f$=0.45, silica gel, CH$_2$Cl$_2$:Et$_2$O:MeOH (60:40:2).

d. N-alpha-N-epsilon-Bis-benzyloxycarbonyl-L-lysyl-L-valyl-L-prolyl-L-valinal A mixture of p-toluenesulfonic acid (0.07 g, 0.37 mmol) and the product of Example 10c in acetone (100 ml) was stirred for 3 hr. at room temperature under a nitrogen atmosphere. The mixture was concentrated in vacuo and the residue was dissolved in EtOAc (50 ml). This solution was washed with 5% aqueous NaHCO$_3$ and brine, dried over MgSO$_4$, filtered and concentrated to give a white foam (0.82 g); TLC, R$_f$=0.46 silica gel, CH$_2$Cl$_2$:MeOH (95:5).

Elemental Analysis: Calculated for C$_{37}$H$_{51}$N$_5$O$_8$.0.4-H$_2$O: C, 63.39; H, 7.44; N, 9.89. Found: C, 63.43; H, 7.43; N, 9.77.

EXAMPLE 11

N-Succinyl-L-leucyl-L-valyl-L-prolyl-L-valinal

Formula (I): R$^1$=—CH(CH$_3$)$_2$; R$^2$=—CH(CH$_3$)$_2$; R$^3$=—CH$_2$CH(CH$_3$)$_2$; R$^4$=—(CH$_2$)$_2$COOH a. N-t-Butyloxycarbonyl-L-leucyl-L-valyl-L-proline t-butyl ester

HOBT (3.10 g, 0.0229 mol) was added to a solution of N-t-butyloxycarbonyl-L-leucine (2.65 g, 0.0115 mol) in dry THF (75 ml) at 0° C. under a nitrogen atmosphere and the reaction mixture was stirred for 15 min. To the resulting solution was added a suspension of the product of Example 6b (5.10 g, 0.0115 mol) in dry THF followed by DCC (2.60 g, 0.0126 mol). The mixture was stirred for 1 hr. at 0° C. and then at room temperature for 4 days. The reaction mixture was filtered and the filtrate concentrated under vacuum. The resulting residue was mixed with cold CHCl$_3$ (500 ml) and filtered. The filtrate was washed successively with 5% aqueous NaHCO$_3$, 20% aqueous citric acid, and brine, dried over Na$_2$SO$_4$, filtered and concentrated to give 3.72 g of the crude product. This material was purified by flash chromatography on silica gel with CHCl$_3$ give the product (2.19 g) as a white waxy solid; TLC, R$_f$=0.50, silica gel, MeOH:CHCl$_3$ (5:95).

b. L-Leucyl-L-valyl-L-proline trifluoroacetic acid salt

Trifluoroacetic acid (18.59 g, 22 ml, 0.163 mol) was added to a solution of the product of Example 11a (3.94 g, 8.2 mol) in dry CH$_2$Cl$_2$ (22 ml) at room temperature under a nitrogen atmosphere. The reaction mixture was stirred for 5 hr. The resulting solution was concentrated under vacuum and the residual amber oil was triturated with Et$_2$O to afford the product (3.07 g) as a white solid.

c. N-(3-Carbomethoxypropionyl)-L-leucyl-l-valyl-L-proline

A solution of the product of Example 11b (3.06 g, 6.9 mmol) in dry CH$_2$Cl$_2$ (60 ml) at room temperature under a nitrogen atmosphere was treated with aqueous 1N NaOH (15 ml). The solution was cooled to 0° C., 3-carbomethoxypropionyl chloride (1.04 g, 6.9 mmol) was added and the reaction mixture was stirred vigorously for 15 min. The reaction mixture was diluted with H$_2$O (50 ml) and adjusted to pH 2 with aqueous 1N HCl. The organic phase was separated and the aqueous phase was extracted with CH$_2$Cl$_2$. The combined organic phases were dried over Na$_2$SO$_4$, filtered and concentrated under vacuum to give the crude product (2.58 g). This material was purified by flash chromatography on silica gel with MeOH:CHCl$_3$ (5:95) to give the product (1.30 g) as a white foam; TLC, R$_f$=0.35, silica gel, MeOH:CHCl$_3$:HOAc (5:94.5:0.5).

d. N-(3-Carbomethoxypropionyl)-L-leucyl-L-valyl-L-prolyl-L-valinal diethylacetal Isobutyl chloroformate (0.38 g, 2.8 mmol) was added to a solution of the product of Example 11c (1.16 g, 2.6 mmol) and N-methylmorpholine (0.40 g, 3.9 mmol) in dry THF (75 ml) at −10° C. under a nitrogen atmosphere. A white precipitate formed immediately. The reaction mixture was stirred for 20 min and then cooled to −40° C. L-Valinal diethylacetal (0.46 g, 2.6 mmol) in dry THF (8 ml) was added in one portion. The reaction mixture was warmed slowly to room temperature and stirred overnight. The resulting mixture was filtered and the filtrate concentrated under vacuum to give a pale yellow oil (1.77 g). The crude material was purified by flash chromatography on silica gel with $CH_2Cl_2$:Et$_2$O:MeOH (60:37:3) as eluent to give the product (1.03 g) as a white foam; TLC, $R_f$=0.52, silica gel, MeOH:CHCl$_3$ (5:95).

e. N-Succinyl-L-leucyl-L-valyl-L-prolyl-L-valinal diethylacetal sodium salt

A stirred solution of the product of Example 11d (0.98 g, 1.6 mmol) in MeOH:H$_2$O (1:1, 30 ml) at room temperature under a nitrogen atmosphere was treated with aqueous 1N NaOH (1.72 ml). The reaction was stirred for 2 hr. and then concentrated under vacuum to give an aqueous solution of the product; TLC, $R_f$=0.14, silica gel, MeOH:CHCl$_3$ (5:95).

f. N-Succinyl-L-leucyl-L-valyl-L-prolyl-L-valinal

Dowex®50WX8-H resin (50 ml) was added to a stirred solution of the product of Example 11e (1.6 mmol) in H$_2$O (100 ml) at room temperature under a nitrogen atmosphere. The reaction mixture was stirred for 2 days. The reaction mixture was filtered and the resin was washed with acetone (50 ml) The filtrate and washes were concentrated under vacuum to remove the acetone. The aqueous mixture was lyophilized to give the product (0.78 g) as a white powder; TLC, $R_f$=0.24, silica gel, MeOH:CHCl$_3$:HOAc (5:94.5:0.5).

EXAMPLE 12

N-alpha-t-Butyloxycarbonyl-N-epsilon-benzyloxycarbonyl-L-lysyl-L-valyl-L-prolyl-L-leucinal Formula I: $R^1$=—$CH_2CH(CH_3)_2$; $R^2$=—$CH(CH_3)_2$; $R^3$=—$(CH_2)_4NHCOO$—$CH_2C_6H_5$; $R^4$=—$OC(CH_3)_3$ a. N-alpha-t-Butyloxycarbonyl-N-epsilon-benzyloxycarbonyl-L-lysyl-L-valyl-L-prolyl-L-leucinol The title compound was prepared as in Example 1e except that a solution of the product of Example 1d (2.2 g, 3.8 mmol) and N-methylmorpholine (0.39 g, 3.8 mmol) in dry THF (20 ml) was used and isobutyl chloroformate (0.525 g, 3.8 mmol) was added followed by a solution of L-leucinol (0.44 g, 3.8 mmol) in dry THF (20 ml). The crude product was purified by flash chromatography on silica gel with MeOH/Et$_2$O (2.5:97.5) followed by MeOH/Et$_2$O (5:95) to give the product (2.16 g); TLC, $R_f$=0.29, silica gel, MeOH:Et$_2$O (5:95).

b. N-alpha-t-Butyloxycarbonyl-N-epsilon-benzyloxycarbonyl-L-lysyl-L-valyl-L-prolyl-L-leucinal The title compound was prepared as in Example 1f, except that oxalyl chloride (0.614 g, 4.8 mmol) in $CH_2Cl_2$ (8.0 ml) was used. DMSO (0.75 g, 9.6 mmol) in $CH_2Cl_2$ (4.0 ml), a solution of the product of Example 12a (1.63 g, 2.4 mmol) in $CH_2Cl_2$ (4.0 ml) and TEA (1.29 g, 9.6 mmol) in $CH_2Cl_2$ (4.0 ml) were successively to give the crude product, which was purified by flash chromatography on silica gel with MeOH:CHCl$_3$ (2.5:97.5) to give the product (1.44 g); TLC, $R_f$=0.53, silica gel, MeOH:CHCl$_3$ (10:90).

EXAMPLE 13

N-(3-Carbomethoxypropionyl)-L-norleucyl-L-valyl-L-prolyl-L-valinal

Formula (I): $R^1$=—$CH(CH_3)_2$; $R^2$=—$CH(CH_3)_2$; $R^3$=—$(CH_2)_3CH_3$; $R^4$=—$(CH_2)_2COOCH_3$ a. N-Benzyloxycarbonyl-L-valyl-L-proline

Trifluoroacetic acid (70 ml, 0.90 mol) was added to a solution of the product of Example 6a (16.5 g, 39.2 mmol) in $CH_2Cl_2$ (100 ml) at room temperature and the resulting mixture was stirred for 3 hr. The solution was diluted with toluene (100 ml) and concentrated under vacuum. The residue was taken up in toluene and reconcentrated 5 times to finally give the product (12.85 g) as a tan solid; TLC, $R_f$=0.45, silica gel, MeOH:CH$_2$Cl$_2$ (5:95).

b. N-Benzyloxycarbonyl-L-valyl-L-prolyl-L-valinal diethylacetal

HOBT (4.21 g, 31.1 mmol) was added to a solution of the product of Example 13a (5.17 g, 15.55 mmol) and L-valinal diethylacetal (2.73 g, 15.55 mmol) in dry THF (75 ml) at 0° C. under a nitrogen atmosphere. This solution was stirred for 15 min and 1-(3-dimethylaminopropyl)-3-ethyl carbodiimide hydrochloride (3.28 g, 17.1 mmol) followed by N-methylmorpholine (2.36 g, 23.3 mmol) were added. The mixture was stirred for 1 hr. at 0° C. and for 3 days at room temperature. The reaction mixture was concentrated in vacuo and the residue was partitioned between EtOAc and H$_2$O. The organic layer was isolated and washed with aqueous 1N HCl, brine, saturated aqueous NaHCO$_3$ and brine, then dried over MgSO$_4$, filtered and concentrated to give a viscous oil. The product was purified by flash chromatography on silica gel with $CH_2Cl_2$:Et$_2$O:MeOH (75:25:0.5) to give a colorless oil (4.4 g); TLC, $R_f$=0.55, silica gel, $CH_2Cl_2$:Et$_2$O:MeOH (75:25:1).

c. L-Valyl-L-prolyl-L-valinal diethylacetal

The product of Example 13b (3.63 g, 7.18 mmol) and 10% Pd/C (0.5 g) in EtOH (75 ml) was hydrogenated on a Parr shaker (3 atm H$_2$). When the theoretical amount of H$_2$ was consumed the mixture was filtered through Celite® and concentrated under vacuum to give the product (2.5 g); TLC, $R_f$=0.3, silica gel, MeOH:CH$_2$Cl$_2$ (1:9).

d. N-Benzyloxycarbonyl-L-norleucyl-L-valyl-L-prolyl-L-valinal diethylacetal HOBT (2.48 g, 18.3 mmol) was added to a solution of the product of Example 13c (3.4 g, 9.15 mmol) and N-benzyloxycarbonyl-L-norleucine (2.43 g, 9.15 mmol) in dry THF (75 ml) at 0°C. under a nitrogen atmosphere. This mixture was stirred for 15 min and 1-(3-dimethylaminopropyl)-3-ethyl carbodiimide hydrochloride (1.93 g, 10.06 mmol) followed by N-methylmorpholine (1.39 g, 13.73 mmol) were added. The mixture was stirred for 1 hr. at 0° C. and then 24 hr. at room temperature. The reaction mixture was concentrated in vacuo and the resulting residue was partitioned between EtOAc and H$_2$O. The isolated organic layer was washed with aqueous 1N HCl, brine, saturated aqueous NaHCO$_3$ and brine, then dried over MgSO$_4$, filtered and concentrated to give the crude product. Purification by flash chromatography on silica gel with CH₂Cl₂:MeOH (95:5) gave the product as a white foam (4.76 g); TLC, R$_f$=0.65 silica gel, CH₂Cl₂:MeOH (9:1).

Elemental Analysis: Calculated for C₃₃H₅₄N₄O₇: C, 64.05; H, 8.79; N, 9.05. Found: C, 63.74; H, 8.78; N, 9.00.

e. L-Norleucyl-L-valyl-L-prolyl-L-valinal diethylacetal

The product of Example 13d (3.70 g, 5.98 mmol) and 10% Pd on carbon (0.25 g) in EtOH (50 ml) was hydrogenated on a Parr shaker (3 atm H₂). After the theoretical amount of H₂ was consumed the mixture was filtered through Celite ® and concentrated under vacuum to give the product (3.2 g); TLC, R$_f$=0.25, silica gel, CH₂Cl₂:MeOH (95:5).

f. N-(3-Carbomethoxypropionyl)-L-norleucyl-L-valyl-L-prolyl-L-valinal diethylacetal A mixture of aqueous 1N NaOH (6.2 ml) and the product of Example 13e (3.0 g, 6.19 mmol) in CH₂Cl₂ (30 ml) was stirred vigorously at 0° C. under a nitrogen atmosphere. After addition of 3-carbomethoxypropionyl chloride (0.93 g, 6.19 mmol) in one batch, the reaction mixture was stirred for 15 min, then diluted with H₂O (25 ml) and adjusted to pH 2 with aqueous 1N HCl. The mixture was extracted with EtOAc. The combined extracts were washed with brine, dried over MgSO₄, filtered and concentrated to give a foam. The product was purified by flash chromatography on silica gel with CH₂Cl₂:Et₂O:MeOH (60:40:2) to give a white foam (2.41 g); TLC, R$_f$=0.45 silica gel, CH₂Cl₂:Et₂O:MeOH (60:40:3).

Elemental Analysis: Calculated for C₃₀H₅₄N₄O₈: C, 60.18; H, 9.09; N, 9.36. Found: C, 60.00; H, 8.91; N, 9.22.

g. N-(3-Carbomethoxypropionyl)-L-norleucyl-L-valyl-L-prolyl-L-valinal

A mixture of the product of Example 13f (0.50 g, 0.835 mmol) and p-toluenesulfonic acid (0.039 g, 0.208 mmol) in acetone (50 ml) was stirred for 3 hr. under a nitrogen atmosphere. The mixture was concentrated in vacuo and the resulting residue was extracted into EtOAc. This solution was washed successively with 5% aqueous NaHCO₃ and brine, dried over MgSO₄, filtered and concentrated to give a foam (0.39 g); TLC, R$_f$=0.5, silica gel, CH₂Cl₂:EtOAc (1:1).

EXAMPLE 14

N-Acetylglycyl-N-epsilon-benzyloxycarbonyl-L-lysyl-L-valyl-L-prolyl-L-valinal

Formula (I): R¹=—CH(CH₃)₂; R²=—CH(CH₃)₂; R³=—(CH₂)₄—NHCOOCH₂C₆H₅; R⁴=—CH₂COCH₃ a. N-alpha-(2-Methylsulfonylethyloxycarbonyl)-N-epsilon-benzyloxycarbonyl-L-lysine To a suspension of N-epsilon-benzyloxycarbonyl-L-lysine (20.3 g, 72.25 mmol) in DMF (300 ml) was added 2-methylsulfonylethyl p-nitrophenyl carbonate (20.85 g, 72.25 mmol). The reaction mixture was stirred overnight at room temperature, TEA (10.0 ml, 72.25 mmol) was added and the mixture was stirred for an additional 24 hr. and filtered. The filtrate was concentrated under vacuum. The residue was dissolved in EtOAc (300 ml) and washed with aqueous 1N HCl and brine. The organic phase was dried over Na₂SO₄, filtered and concentrated under vacuum to give a viscous yellow oil. The crude product was purified by flash chromatography on silica gel with CHCl₃, MeOH:CHCl₃ (2:98) and finally MeOH:CHCl₃ (5:95) to give the product (20.67 g); TLC, R$_f$=0.29, silica gel, MeOH:CHCl₃:HOAc (9.5:90:0.5).

b. N-alpha-(2-methylsulfonylethylcarbonyl)-N-epsilon-benzyloxycarbonyl-L-lysyl-L-valyl-L-proline t-butyl ester A solution of the product of Example 14a (2.00 g, 4.65 mmol) in dry THF (25 ml) under a nitrogen atmosphere was cooled to −20° C. N-methylmorpholine (0.51 ml, 4.65 mmol) was added followed by isobutyl chloroformate (0.6 ml, 4.65 mmol). The mixture was stirred for 10 min and then cooled to −50° C. A solution of the product of Example 6b (1.25 g, 4.65 mmol) in dry THF (25 ml) was added dropwise. The solution was allowed to warm to room temperature slowly and was stirred overnight. The reaction mixture was filtered and the filtrate concentrated under vacuum. The crude product was purified by flash chromatography on silica gel with MeOH:CHCl₃ (5:95) to give the product (2.47 g); TLC, R$_f$=0.25, silica gel, MeOH:CHCl₃ (5:95).

c. N-alpha-(2-Methylsulfonylethylcarbonyl)-N-epsilon-benzyloxycarbonyl-L-lysyl-L-valyl-L-proline Trifluoroacetic acid (2.5 ml, 32.5 mmol) was added to a solution of the product of Example 14b (1.0 g, 1.47 mmol) in CH₂Cl₂ (2.5 ml). The reaction mixture was stirred for 3.5 hr. and then concentrated under vacuum. The resulting syrup was triturated repeatedly with Et₂O to give the product (0.96 g).

d. N-alpha-(2-Methylsulfonylethylcarbonyl)-N-epsilon-benzyloxycarbonyl-L-lysyl-L-valyl-L-prolyl-L-valinal diethylacetal The title compound was prepared as in Example 6j except that the product of Example 14c (0.96 g, 1.53 mmol) in THF (10 ml) was used, and N-methylmorpholine (0.17 ml, 1.53 mmol), isobutyl chloroformate (0.20 ml, 1.53 mmol) and L-valinal diethylacetal (0.27 g, 1.53 mmol) in THF (10 ml) were added successively. The crude product was purified by flash chromatography on silica gel with MeOH:CHCl₃ (2.5:97.5) and then MeOH:CHCl₃ (5:95) to give the product (0.65 g); TLC, R$_f$=0.40, silica gel, MeOH:CHCl₃ (10:90).

e. N-alpha-(2-Methylsulfonylethyloxycarbonyl)-N-epsilon-benzyloxycarbonyl-L-lysyl-L-valyl-L-prolyl-L-valinal diethylacetal (Alternate synthesis)

1-(3-Dimethylaminopropyl)-3-ethyl carbodiimide hydrochloride (1.74 g, 8.88 mmol) and N-methylmorpholine (1.34 ml, 12.12 mmol) were added to a solution of the product of Example 13c (3.0 g, 8.08 mmol). The product of Example 14a (3.84 g, 8.08 mmol) and HOBT (2.18 g, 16.16 mmol) in CH₂Cl₂ (60 ml) at 0° C. under a nitrogen atmosphere. The reaction mixture was stirred at 0° C. for 1 hr. and then at room temperature overnight. The reaction mixture was concentrated in vacuo and the residue was taken up in EtOAc, washed with H₂O, aqueous 1N HCl, brine, 5% aqueous NaHCO₃ and brine, dried over MgSO$_4$. This solution was filtered and concentrated to give the crude product which was purified by flash chromatography on silica gel with MeOH:CH$_2$Cl$_2$ (5:95) to give the product (5.0 g); TLC, R$_f$=0.60 g, silica gel, MeOH:CH$_2$Cl$_2$ (5:95).

f.
N-epsilon-benzyloxycarbonyl-L-lysyl-L-valyl-L-prolyl-L-valinal diethylacetal Aqueous 4N NaOH (0.315 ml) was added to a solution of the product of Example 14d (0.495 g, 0.63 mmol) in MeOH (6 ml). The reaction mixture was stirred for 5 min. Aqueous 1N HCl (1.89 ml) was added and the reaction mixture was concentrated under vacuum. The residue was dissolved in EtOAc (30 ml), washed with aqueous 5% NaHCO$_3$ and brine, dried over Na$_2$SO$_4$, filtered and concentrated under vacuum to give the product (0.395 g); TLC, R$_f$=0.5, silica gel, MeOH:CHCl$_3$ (10:90).

g.
N-Acetylglycyl-N-epsilon-benzyloxycarbonyl-L-lysyl-L-valyl-L-prolyl-L-valinal diethylacetal N-acetylglycine (0.073 g, 0.62 mmol) and DCC (0.14 g, 0.68 mmol) was added to a solution of the product of Example 14f (0.395 g, 0.62 mmol) in DMF (2 ml). The reaction mixture was stirred overnight at room temperature. The reaction mixture was filtered and concentrated in vacuo. The residue was dissolved in CHCl$_3$, filtered and concentrated under vacuum to give the crude product which was purified by flash chromatography on silica gel with MeOH:CHCl$_3$ (5:95) to give the product (0.37 g); TLC, R$_f$=0.44, silica gel, MeOH:CHCl$_3$:CHCl$_3$:HOAc (9.5/90/0.5).

h.
N-Acetylglycyl-N-epsilon-benzyloxycarbonyl-L-lysyl-L-valyl-L-prolyl-L-valinal Dowex ®50WX8-H resin (2 ml) was added to a solution of the product of Example 14 g (0.30 g, 0.41 mmol) in acetone:H$_2$O (1:4, 10 ml) and the reaction mixture was stirred for 48 hr. The reaction mixture was filtered and the filtrate was concentrated under vacuum to give the product (0.13 g); TLC, R$_f$=0.35, silica gel, MeOH/CHCl$_3$ (10:90).

EXAMPLE 15
N-alpha-(2-Methylsulfonylethyloxycarbonyl)-N-epsilon-benzyloxycarbonyl-L-lysyl-L-valyl-L-prolyl-L-valinal Formula I: R$^1$=—CH(CH$_3$)$_2$; R$^2$=—CH(CH$_3$)$_2$; R$^3$=—(CH$_2$)$_4$NHCO$_2$CH$_2$C$_6$H$_5$; R$^4$=—O(CH$_2$)$_2$SO$_2$CH$_3$ p-Toluenesulfonic acid (0.42 g, 2.2 mmol) was added to a solution of the product of Example 14d in acetone (450 ml) and the reaction mixture was stirred for 2 hr. The reaction mixture was concentrated under vacuum. The residue was dissolved in EtOAc (100 ml), washed with aqueous 5% NaHCO$_3$ and brine, dried over Na$_2$SO$_4$, filtered and concentrated under vacuum to give the product (0.90 g); TLC, R$_f$=0.43, silica gel, MeOH:CHCl$_3$ (5:95).

Elemental Analysis: Calculated for C$_{33}$H$_{51}$N$_5$O$_{10}$S.0.5H$_2$O: C, 55.14; H, 7.29; N, 9.74. Found: C, 55.21; H, 7.41; N, 9.24.

EXAMPLE 16
N-Benzyloxycarbonyl-L-norleucyl-L-valyl-L-prolyl-L-valinal

Formula (I): R$^1$=—CH(CH$_3$)$_2$; R$^2$=—CH(CH$_3$)$_2$; R$^3$=—(CH$_2$)$_3$CH$_3$; R$^4$=—OCH$_2$C$_6$H$_5$ A mixture of the product of Example 13d (0.75 g, 1.21 mmol) and p-toluenesulfonic acid (0.066 g, 0.35 mmol) in acetone (100 ml) was stirred for 3 hr. at room temperature. The mixture was concentrated under vacuum and the residue was dissolved in EtOAc. This solution was washed successively with 5% aqueous NaHCO$_3$ and brine, dried over MgSO$_4$, filtered and concentrated to give a glass. Purification by reverse-phase flash chromatography with MeOH:H$_2$O (7:3) gave a white powder (0.414 g); TLC, R$_f$=0.5, C$_{18}$ reverse-phase, MeOH:H$_2$O (7:3).

EXAMPLE 17
N-Succinyl-L-norleucyl-L-valyl-L-prolyl-L-valinal

Formula (I): R$^1$=—CH(CH$_3$)$_2$; R$^2$=—CH(CH$_3$)$_2$; R$^3$=—(CH$_2$)$_3$CH$_3$; R$^4$=—(CH$_2$)$_2$COOH A mixture of the product of Example 13f (1.81 g, 3.02 mmol) and aqueous 1N NaOH (3.13 ml) in MeOH:H$_2$O (1:1, 56 ml) was stirred for 2 hr. at room temperature under a nitrogen atmosphere. The MeOH was removed under vacuum. Acetone (30 ml), H$_2$O (200 ml), and Dowex ®50WX8-H resin (120 ml) were added and the mixture was stirred for 24 hr. The mixture was filtered and the resin was washed with acetone. The combined filtrates were concentrated to remove the acetone and the aqueous solution was lyophilized to give a fluffy white solid (1.41 g).

Elemental Analysis: Calculated for C$_{25}$H$_{42}$N$_4$O$_7$: C, 58.80; H, 8.29; N, 10.97. Found: C, 58.48; H, 8.29; N, 10.67.

EXAMPLE 18
N-alpha-Trimethylacetyl-N-epsilon-benzyloxycarbonyl-L-lysyl-L-valyl-L-prolyl-L-valinal Formula (I): R$^1$=—CH(CH$_3$)$_2$; R$^2$=—CH(CH$_3$)$_2$; R$^3$=—(CH$_2$)$_4$—NHCOOCH$_2$C$_6$H$_5$; R$^4$=—C(CH$_3$)$_3$ a.
N-alpha-Trimethylacetyl-N-epsilon-benzyloxycarbonyl-L-lysyl-L-valyl-L-proline A mixture of the product of Example 6d (3.54 g, 5.99 mmol) in CH$_2$Cl$_2$ (35 ml) and aqueous 1N NaOH (12 ml) was vigorously stirred at 0° C. Trimethylacetyl chloride (0.73 g, 5.92 mmol) was added in one batch. The reaction mixture was stirred for 15 min at 0° C., then diluted with H$_2$O (25 ml) and the pH adjusted to 2 with aqueous 1N HCl. The mixture was then extracted with EtOAc. The combined organic layers were washed with brine, dried over MgSO$_4$, filtered and concentrated to give the product as an off-white foam (3.39 g); TLC, R$_f$=0.35, silica gel, MeOH:CH$_2$Cl$_2$:HOAc (5:95:1).

b.
N-alpha-Trimethylacetyl-N-epsilon-benzyloxycarbonyl-L-lysyl-L-valyl-L-prolyl-L-valinal diethylacetal HOBT (1.63 g, 12.09 mmol) was added to a solution of the product of Example 18a (3.39 g, 6.04 mmol) and L-valinal diethylacetal (1.06 g, 6.04 mmol) in dry THF (65 ml) at 0° C. under a nitrogen atmosphere and the mixture was stirred for 15 min. To the resulting solution was added 1-(3-dimethylaminopropyl)-3-ethyl carbodiimide hydrochloride (1.39 g, 7.25 mmol) followed by N-methylmorpholine (0.92 g, 9.06 mmol). The mixture was stirred for 1 hr. at 0° C. and then for 24 hr. at room temperature. The reaction mixture was concentrated in vacuo and the resulting residue was partitioned between EtOAc and $H_2O$. The organic layer was isolated and washed with aqueous 1N HCl, brine, saturated aqueous $NaHCO_3$ and brine then dried over $MgSO_4$, filtered and concentrated to give a crude foam. The product was purified by flash chromatography on silica gel with $CH_2Cl_2$:$Et_2O$:MeOH (60:40:2) to give a white foam (2.40 g); TLC, $R_f$=0.45 silica gel, $CH_2Cl_2$:$Et_2O$:MeOH (60:40:2).

c. N-alpha-Trimethylacetyl-N-epsilon-benzyloxycarbonyl-L-lysyl-L-valyl-L-prolyl-L-valinal p-Toluenesulfonic acid (0.25 g, 1.3 mm) was added to a solution of the product of Example 18b (2.3 g, 3.2 mmol) in acetone (100 ml) at room temperature under a nitrogen atmosphere and the mixture was stirred for 3 hr. The reaction mixture was then concentrated in vacuo and the resulting residue was dissolved in EtOAc. This solution was washed with 5% aqueous $NaHCO_3$ and brine, dried over $MgSO_4$, filtered and concentrated to give a white foam. The product was purified by reverse-phase flash chromatography with MeOH:$H_2O$ (7:3) to give a white powder (1.78 g); TLC, $R_f$=0.60, reverse-phase $C_{18}$, MeOH:$H_2O$ (7:3).

Elemental Analysis: Calculated for $C_{34}H_{53}N_5O_7 \cdot 0.5 H_2O$: C, 62.55; H, 8.33; N, 10.72. Found: C, 62.17; H, 8.52; N, 10.41.

EXAMPLE 19

N-alpha-(3-Carbomethoxypropionyl)-N-epsilon-benzyloxycarbonyl-L-lysyl-L-phenylalanyl-L-prolyl-L-valinal Formula (I): $R^1$=—CH(CH$_3$)$_2$; $R^2$=—CH$_2$C$_6$H$_5$; $R^3$=—(CH$_2$)$_4$NHCOOCH$_2$C$_6$H$_5$; $R^4$=—(CH$_2$)$_2$CO$_2$CH$_3$ a. N-Benzyloxycarbonyl-L-phenylalanyl-L-proline t-butyl ester HOBT (2.70 g, 20 mmol) was added to a solution of N-benzyloxycarbonyl-L-phenylalanine (2.99 g, 10 mmol) in dry DMF (100 ml) at 0° C. under a nitrogen atmosphere and the mixture was stirred for 15 min. A solution of DCC (2.26 g, 11 mmol) in dry DMF (20 ml) was added and the mixture was stirred for 5 min. at 0° C. A solution of L-proline t-butyl ester (1.71 g, 10 mmol) in dry DMF (30 ml) was then added. The mixture was stirred at 0° C. for 1 hr. and at room temperature for an additional 48 hr. The reaction mixture was filtered and the filtrate concentrated under vacuum. The resulting residue was mixed with cold EtOAc (50 ml) and filtered. The filtrate was washed successively with 20% aqueous citric acid, brine, 5% aqueous NaHCO$_3$, and brine. The organic phase was dried over Na$_2$SO$_4$, filtered and concentrated to give the product (3.96 g) as a thick yellow syrup; TLC, $R_f$=0.60, silica gel, EtOAc:CHCl$_3$ (15:85).

b. L-Phenylalanyl-L-proline t-butyl ester

A mixture of the product of Example 19a (3.80 g, 11.9 mmol) and 10% Pd/C (1 g) in EtOH (150 ml) was placed on a Parr apparatus under H$_2$ (60 psi) and shaken for 9 hr. at room temperature. The mixture was filtered through Celite ® and the filtrate was concentrate under vacuum to give the product (2.47 g).

c. N-alpha-t-Butyloxycarbonyl-N-epilson-benzyloxycarbonyl-L-lysyl-L-phenylalanyl-L-proline t-butyl ester HOBT (3.16 g, 23.4 mmol) was added to a solution of N-alpha-t-butyloxycarbonyl-N-epsilon-benzyloxycarbonyl-L-lysine (4.45 g, 11.7 mmol) in dry THF (50 ml) at 0° C. under nitrogen atmosphere and the mixture was stirred for 15 min. A solution of the product of Example 19b (3.16 g, 11.7 mmol) in dry THF (30 ml) was then added and the mixture was stirred for an additional 5 min. Then DCC (2.66 g, 12.87 mmol) was added and the mixture was stirred for 1 hr. at 0° C. and then at room temperature for 36 hr. The reaction mixture was filtered and the filtrate was concentrated under vacuum. The residue was taken up in CHCl$_3$ (75 ml) and this solution was cooled to 0° C. and filtered. The filtrate was washed successively with 20% aqueous citric acid, 5% aqueous NaHCO$_3$, and brine. The organic phase was dried over Na$_2$SO$_4$, filtered, and concentrated to give the crude product (5.95 g). Purification by flash chromatography on silica gel with MeOH:CH$_2$Cl$_2$ (2.5:97.5) gave the product (4.63 g); TLC, $R_f$=0.7, silica gel, MeOH:CH$_2$Cl$_2$ (5:95).

d. N-epsilon-Benzyloxycarbonyl-L-lysyl-L-phenylalanyl-L-proline trifluoroacetic acid salt Trifluoroacetic acid (30 ml) was added to a solution of the product of Example 19c (4.42 g, 8.74 mmol) in dry CH$_2$Cl$_2$ (30 ml) under nitrogen. The mixture was stirred at room temperature for 5 hr. Toluene (30 ml) was added and the resulting mixture was concentrated under vacuum to give the product (3.96 g); TLC, $R_f$=0.1 silica gel, MeOH:CH$_2$Cl$_2$:HOAc (5:95:0.5).

e. N-alpha-(3-Carbomethoxypropionyl)-N-epsilon-benzyloxycarbonyl-L-lysyl-L-phenylalanyl-L-proline A mixture of the product of Example 19d (3.75 g, 6.36 mmol) in CH$_2$Cl$_2$ (43 ml) and aqueous 1N NaOH (12.7 ml) was stirred vigorously at 0° C. while 3-carbomethoxypropionyl chloride (0.783 ml, 6.36 mmol) was added in one portion. The resulting mixture was stirred vigorously at 0° C. for 12 min. The mixture was then diluted with water and adjusted to pH 2 with 1N HCl. The organic layer was collected and the aqueous layer was extracted twice with CH$_2$Cl$_2$. The organic extracts were combined, dried over Na$_2$SO$_4$, filtered and concentrated to give the product (3.46 g); TLC, $R_f$=0.5, silica, CH$_3$OH:CH$_2$Cl$_2$:HOAc (5:95:0.5).

f. N-alpha-(3-Carbomethoxypropionyl)-N-epsilon-benzyloxycarbonyl-L-lysyl-L-phenylalanyl-L-prolyl-L-valinal diethylacetal Isobutyl chloroformate (0.66 ml, 5.15 mmole) was added to a solution of the product of Example 19e (3.41 g, 5.15 mmole) and N-methylmorpholine (0.563 ml, 5.15 mmole) in dry THF (46 ml) at −15° C. under a N$_2$ atmosphere. The reaction mixture was stirred at −15° C. for 30 min. and then cooled to −40° C. A solution of L-valinal diethylacetal (0.904 g, 5.15 mmol) in dry THF (4 ml) was added dropwise. The resulting mixture was allowed to warm slowly to room temperature and was stirred for 24 hr. The reaction mixture was filtered and the filtrate was concentrated under vacuum to give a residue which was purified by flash chromatography on silica gel with $CH_2Cl_2$:MeOH (97:3) to give the product (2.51 g); TLC, $R_f=0.45$, MeOH:$CH_2Cl_2$ (5:95).

Elemental Analysis: Calculated for $C_{42}H_{60}N_5O_{10}.0.5\text{-}H_2O$: C, 62.75; H, 7.65; N, 8.71. Found: C, 62.82; H, 7.50; N, 8.48.

g.
N-alpha-(3-Carbomethoxypropionyl)-N-epsilon-benzyloxycarbonyl-L-lysyl-L-phenylalanyl-L-prolyl-L-valinal A mixture of the product of Example 19f (0.5 g, 0.628 mmol), acetone (100 ml) and p-toluenesulfonic acid monohydrate (0.026 g, 0.125 mmol) was stirred at room temperature under nitrogen for 5 hr. The mixture was concentrated under vacuum. The residue was dissolved in EtOAc and washed with 5% aqueous $NaHCO_3$. The organic layer was dried over $Na_2SO_4$, filtered, and concentrated under vacuum to give the product (0.45 g); TLC, $R_f=0.31$, silica gel, MeOH:$CH_2Cl_2$ (5:95).

Elemental Analysis: Calculated for $C_{38}H_{51}N_5O_9.0.5\text{-}H_2O$: C, 62.45; H, 7.17; N, 9.58. Found: C, 62.37; H, 7.10; N, 9.42.

EXAMPLE 20

N-alpha-[3-(Methylsulfonylaminocarbonyl)propionyl]-N-epsilonbenzyloxycarbonyl-L-lysyl-L-valyl Formula (I): $R^1=-CH(CH_3)_2$; $R^2=-CH(CH_3)_2$; $R^3=-(CH_2)_4\text{-NHCOOCH}_2C_6H_5$; $R^4=-(CH_2)_2CONHSO_2CH_3$ a.
N-alpha-Succinyl-N-epsilon-benzyloxycarbonyl-L-lysyl-L-valyl-L-prolyl-L-valinal diethylacetal A mixture of the product of Example 6j (3.0 g, 4.0 mmol) in MeOH:$H_2O$ (1:1, 40 ml) and aqueous 1N NaOH (4.4 ml) was stirred at room temperature for 1.5 hr. The solution was acidified with aqueous 1N HCl (5 ml) and extracted with EtOAc. The organic solution was dried over $Na_2SO_4$, filtered and concentrated under vacuum to give the product (2.66 g, 0.36 mmol); TLC, $R_f=0.55$, MeOH:$CHCl_3$:HOAc (9.5/90/0.5).

b.
N-alpha-[3-(Methylsulfonylaminocarbonyl)propionyl]-N-epsilon-benzyloxycarbonyl-L-lysyl-L-valyl-L-prolyl-L-valinal diethylacetal A solution of the product of Example 20a (0.5 g, 0.682 mmol), methanesulfonamide (65 mg, 0.682 mmol), dicyclohexyl carbodiimide (140 mg, 0.68 mmol) and 4-dimethylaminopyridine (83 mg, 0.68 mmol) in dry $CH_2Cl_2$ (15 ml) was stirred overnight at room temperature. The dicyclohexylurea was removed by filtration and the filtrate concentrated under vacuum to give the crude product (0.73 g). The product was purified by flash chromatography on silica gel with MeOH:$CHCl_3$ (3:97) to give a white solid (0.33 g); TLC, $R_4=0.4$, silica gel, $CH_3OH$:$CHCl_3$ (3:97).

c.
N-alpha-[3-(Methylsulfonylaminocarbonyl)propionyl]-N-epsilon-benzyloxycarbonyl-L-lysyl-L-valyl-L-prolyl-L-valinal A mixture of the product of Example 20b (0.3 g, 0.37 mmol) and Dowex® 50WX8-H resin (12.8 ml) in acetone/water (1:5, 24 ml) was stirred at room temperature for 48 hr. The resin was removed by filtration and the filtrate concentrated under vacuum to give an aqueous solution which was lyophilized to give the product (0.18 g) as a white solid; TLC, $R_f=0.2$, silica gel, $CH_3OH$:$H_2O$ (5:95).

EXAMPLE 21

N-alpha-Succinyl-N-epsilon-benzyloxycarbonyl-L-lysyl-L-phenylalanyl-L-prolyl-L-valinal Formula I: $R^1=-CH(CH_3)_2$; $R^2=-CH_2C_6H_5$; $R^3=-(CH_2)_4\text{NHCOOCH}_2C_6H_5$; $R^4=-(CH_2)_2COOH$ A mixture of the product of Example 19f (1.0 g, 1.25 mmol) in $CH_3OH$:$H_2O$ (1:1, 26 ml) and aqueous 1N NaOH (1.31 ml) was stirred at room temperature for 4 hr. The methanol was removed under vacuum to give an aqueous solution (13 ml) of N-alpha-succinyl-N-epsilon-benzyloxycarbonyl-L-lysyl-L-phenylalanyl-L-prolyl-L-valinal diethylacetal which was immediately added to a stirred mixture of Dowex® 50WX8-H resin (46.3 g) in water (94 ml) and acetone (11.8 ml). This mixture was stirred for 48 hr. at room temperature. The mixture was filtered and the resin was washed with acetone. The filtrate and washings were combined, diluted with water (50 ml) and concentrated under vacuum to give an aqueous solution (100 ml) which was lyophilized to give the product (0.54 gm) as a white solid; TLC, $R_f=0.27$, silica gel, MeOH:$CH_2Cl_2$ (5:95).

EXAMPLE 22

N-alpha-Succinyl-N-epsilon-(2,4-dichlorobenzoyl)-L-lysyl-L-valyl-L-prolyl-L-valinal Formula I. $R^1=-CH(CH_3)_2$; $R^2=-CH(CH_3)_2$; $R^3=-(CH_2)_4\text{NHCOC}_6H_3Cl_2$; $R^4=-(CH_2)_2COOH$ a.
N-alpha-t-Butyloxycarbonyl-L-lysyl-L-valyl-L-proline t-butyl ester A mixture of the product of Example 6c (5.0 g, 7.9 mmol) and 10% Pd/C (1 g) in ethanol (50 ml) was shaken on a Parr apparatus under hydrogen (60 psi) for 5 hr. The reaction mixture was filtered and concentrated under vacuum to give the crude product. This product was purified by flash chromatography on silica gel with MeOH:$CHCl_3$ (10:90) to give a white foam (4.5 g); TLC, $R_f=0.3$, silica gel, $CHCl_3$:MeOH (90:10).

b.
N-alpha-t-Butyloxycarbonyl-N-epsilon-(2,4-dichlorobenzoyl)-L-lysyl-L-valyl-L-proline t-butyl ester 2,4-Dichlorobenzoyl chloride (1.87 g, 8.9 mmol) was added to a solution of the product of Example 22a (4.52 g, 8.9 mmol) and N-methylmorpholine (1.0 g, 10 mmol) in $CH_2Cl_2$ (50 ml) at 5° C. The resulting mixture was stirred for 1 hr. at 5° C. and overnight at room temperature. The mixture was diluted with $CH_2Cl_2$ (200 ml) and washed successively with 20% citric acid, saturated NaHCO$_3$ and brine. The organic layer was dried over Na$_2$SO$_4$, filtered and concentrated under vacuum and the product was purified by flash chromatography on silica gel with MeOH:CHCl$_3$ (5:95) to give a white foam (2.2 g); TLC, R$_f$=0.6, silica gel, MeOH:CHCl$_3$ (5:95).

c.
N-epsilon-(2,4-dichlorobenzoyl)-L-lysyl-L-valyl-L-proline trifluoroacetic acid salt A mixture of trifluoroacetic acid (7.3 g, 6.4 mmol) and the product of Example 22b (2.2 g, 3.7 mmol) in CH$_2$Cl$_2$ (5 ml) was stirred for 5 hr. at room temperature. The mixture was concentrated under vacuum and the residue was triturated with Et$_2$O. The solid product was isolated by filtration and dried under vacuum to give a white solid (1.73 g).

d.
N-alpha-(3-Carbomethoxypropionyl)-N-epsilon-(2,4-dichlorobenzoyl)-L-lysyl-L-valyl-L-proline A vigorously stirred solution of the product of Example 22c (1.73 g, 2.7 mmol) in CH$_2$Cl$_2$ (10 ml) at 5° C. was treated with aqueous 1N NaOH (2.7 ml). 3-Carbomethoxypropionyl chloride (0.41 g, 2.7 mmol) was added and the solution stirred for an additional 15 min. The reaction mixture was diluted with H$_2$O (50 ml) and the pH was adjusted to 2 with aqueous 1N HCl. The organic phase was separated and the aqueous phase was extracted twice with CH$_2$Cl$_2$. The combined organic phases were dried over Na$_2$SO$_4$ and concentrated under vacuum to give the product (1.32 g) as a pale yellow foam; TLC, R$_f$=0.10, silica gel, MeOH:CHCl$_3$, (5:95).

e.
N-alpha-(3-Carbomethoxypropionyl)-N-epsilon-(2,4-dichlorobenzoyl)-L-lysyl-L-valyl-L-prolyl-L-valinal diethylacetal Isobutyl chloroformate (0.29 g, 2.0 mmol) was added to a solution of the product of Example 22d (1.32 g, 2.0 mmol) and N-methylmorpholine (0.210 g, 2.0 mmol) in CH$_2$Cl$_2$ (15 ml) at −10° C. under a nitrogen atmosphere. The reaction mixture was stirred at −10° C. for 30 min. and then cooled to −40° C. and L-valinal diethylacetal (0.37 g, 2.0 mmol) was added in one portion. The mixture was stirred at −40° C. for 1 hr. and then at room temperature for 2 hr. The mixture was concentrated under vacuum and the product was purified by flash chromatography on silica gel with MeOH:CHCl$_3$ (3:97) to give a white solid (980 mg); TLC, R$_f$=0.7, silica gel, MeOH:CHCl$_3$ (5:95).

f.
N-alpha-Succinyl-N-epsilon-(2,4-dichlorobenzoyl)-L-lysyl-L-valyl-L-prolyl-L-valinal A mixture of the product of Example 22e (970 mg, 1.2 mmol) in H$_2$O:MeOH (1:1, 30 ml) and aqueous 1N NaOH (1.2 ml) was stirred at room temperature for 1.5 hr. The methanol was removed under vacuum. Dowex® 50WX8-H resin (50 ml), H$_2$O (100 ml) and acetone (20 ml) were added and the mixture was stirred at room temperature for 24 hr. The reaction mixture was filtered and the resin was washed with acetone. The combined filtrates were concentrated under vacuum to remove acetone and the aqueous solution was lyophilized to give the product (700 mg) as a white solid; TLC R$_f$=0.4, silica gel, HOAc:MeOH:CHCl$_3$ (0.25:10:89.75).

EXAMPLE 23

N-alpha-(2,4-Dichlorobenzoyl)-N-epsilon-benzyloxycarbonyl-L-lysyl-L-valyl-L-prolyl-L-valinal Formula (I): R$^1$=—CH(CH$_3$)$_2$; R$^2$=—CH(CH$_3$)$_2$; R$^3$=—(CH$_2$)$_4$NHCO$_2$-CH$_2$C$_6$H$_5$; R$^4$=—C$_6$H$_3$Cl$_2$ a.
N-alpha-(2,4-Dichlorobenzoyl)-N-epsilon-benzyloxycarbonyl-L-lysyl-L-valyl-L-prolyl-L-valinal diethylacetal 2,4-Dichlorobenzoyl chloride (0.132 g, 0.632 mmol) was added to a stirred mixture of the product of Example 14f (0.40 g, 0.632 mmol) in CH$_2$Cl$_2$ (15 ml) and N-methylmorpholine (0.5 ml) at 0° C. under a nitrogen atmosphere. The reaction mixture was stirred for 30 min. and then poured into aqueous 1N HCl and extracted with EtOAc. The combined organic extracts were washed with brine, dried over MgSO$_4$, filtered and concentrated to give the product. This oil was purified by flash chromatography on silica gel with MeOH:CH$_2$Cl$_2$ (3:97) to give a colorless oil (0.41 g); TLC, R$_f$=0.60, silica gel, MeOH:CH$_2$Cl$_2$ (5:95).

b.
N-alpha-2,4-Dichlorobenzoyl-N-epsilon-benzyloxycarbonyl-L-lysyl-L-valyl-L-prolyl-L-valinal The product of Example 23a was treated with p-toluenesulfonic acid as described in Example 10d to give a white foam (0.34 g); TLC, R$_f$=0.5, silica gel, CH$_2$Cl$_2$:MeOH (95:5).

Elemental Analysis: Calculated for C$_{36}$H$_{47}$N$_5$Cl$_2$O$_7$.H$_2$O: C, 57.59; H, 6.57; N, 9.32. Found: C, 57.75; H, 6.50; N, 9.06.

EXAMPLE 24

N-alpha-(4-Carboxybenzoyl)-N-epsilon-benzyloxycarbonyl-L-lysyl-L-valyl-L-prolyl-L-valinal Formula (I): R$^1$=—CH(CH$_3$)$_2$; R$^2$=—CH(CH$_3$)$_2$; R$^3$=—(CH$_2$)$_4$-NHCOCH$_2$C$_6$H$_5$; R$^4$=—C$_6$H$_4$CO$_2$H a.
N-alpha-(4-Carbomethoxybenzoyl)-N-epsilon-benzyloxycarbonyl-L-lysyl-L-valyl-L-prolyl-L-valinal diethylacetal 1-(3-Dimethylaminopropyl)-3-ethylcarbodiimide hydrochloride (0.133 g, 0.69 mmol) and N-methylmorpholine (0.1 ml, 0.95 mmol) were added to a solution of the product of Example 14f (0.40 g, 0.632 mmol), p-carbomethoxy benzoic acid (0.114 g, 0.632 mmol) and HOBT (0.17 g, 1.26 mmol) in dry THF (20 ml) at 0° C. under a N$_2$ atmosphere. The reaction mixture stirred at 0° C. for 1 hr. and then at room temperature overnight. The reaction mixture was concentrated under vacuum. The residue was taken up in EtOAc washed with aqueous 1N HCl, brine, 5% aqueous NaHCO$_3$ and brine, dried over MgSO$_4$, filtered and concentrated to give the crude product. Purification by flash chromatography on silica gel with CH$_2$Cl$_2$:MeOH (95:5) gave a white foam (0.32 g); TLC, R$_f$=0.6, silica gel, CH$_2$Cl$_2$:MeOH (95:5).

b.
N-alpha-(4-Carboxybenzoyl)-N-epsilon-benzyloxycarbonyl-L-lysyl-L-valyl-L-prolyl-L-valinal 1N NaOH (0.5 mmol) was added to the product of Example 24a (0.32 g, 0.40 mmol) in MeOH (5 ml) and H₂O (3 ml) at room temperature under N₂ and the mixture was stirred overnight. The MeOH was removed in vacuo, acetone (10 ml) and 1N HCl (10 ml) were added and the mixture was stirred overnight. The acetone was removed under vacuum and the aqueous layer was extracted repeatedly with EtOAc. The combined organic extracts were washed with brine, dried over MgSO₄ and concentrated to give the crude product. Purification by flash chromatography on silica with MeOH:CH₂Cl₂:HOAc (5:95:0.5) gave a white foam (0.210 g); TLC, $R_f$=0.65, silica gel, MeOH:CH₂Cl₂:HOAc (10:90:1).

EXAMPLE 25

N-alpha-(2-Carboxybenzoyl)-N-epsilon-benzyloxycarbonyl-L-lysyl-L-valyl-L-propyl-L-valinal Formula (I): $R^1$=—CH(CH₃)₂; $R^2$=—CH(CH₃)₂; $R^3$=—(CH₂)₄NHCOCH₂-C₆H₅; $R^4$=—C₆H₄CO₂H a. N-alpha-(2-Carboxybenzoyl)-N-epsilon-benzyloxycarbonyl-L-lysyl-L-valyl-L-prolyl-L-valinal diethylacetal Phthalic anhydride (0.117 g, 0.79 mmol) was added to a solution of the product of Example 14f (0.50 g, 0.79 mmol) in acetonitrile (10 ml). The reaction mixture was stirred overnight at room temperature then concentrated under vacuum to give the crude product. This compound was purified by flash chromatography on silica gel with CH₂Cl₂:MeOH:HOAc (95:5:1) to give an oil (0.42 g); TLC, $R_f$=0.5, silica gel, CH₂Cl₂:MeOH:HOAc (95:5:1).

b. N-alpha-(2-Carboxybenzoyl)-N-epsilon-benzyloxycarbonyl-L-lysyl-L-valyl-L-prolyl-L-valinal The product of Example 25a was reacted with p-toluenesulfonic acid as described in Example 10d. The product was purified by flash chromatography on a reverse-phase C₁₈ column with THF:H₂O (1:1) to give a white foam (0.15 g); TLC, $R_f$=0.75, reverse-phase (C₁₈), THF:H₂O (1:1).

EXAMPLE 26

N-alpha-(4-Phenylbenzoyl)-N-epsilon-benzyloxycarbonyl-L-lysyl-L-valyl-L-prolyl-L-valinal Formula (I): $R^1$=—CH(CH₃)₂; $R^2$=—CH(CH₃)₂; $R^3$=—(CH₂)₄NHCO₂-CH₂C₆H₅; $R^4$=—C₆H₄C₆H₅ a. N-alpha-(4-Phenylbenzoyl)-N-epsilon-benzyloxycarbonyl-L-lysyl-L-valyl-L-prolyl-L-valinal diethylacetal 1-(3-Dimethylaminopropyl)-3-ethyl carbodiimide hydrochloride (0.133 g, 0.69 mmol) and N-methylmorpholine (0.1 ml, 0.95 mmol) were added to a solution of the product of Example 14f (0.40 g, 0.63 mmol), 4-phenylbenzoic acid (0.125 g, 0.63 mmol) and HOBT (0.171 g, 1.26 mmol) in CH₂Cl₂ (20 ml), at 0° C. under a N₂ atmosphere. The reaction mixture was stirred at 0° C. for 1 hr. and then at room temperature overnight. The reaction mixture was poured into aqueous 1N HCl and the organic layer was isolated and washed with brine, 5% aqueous NaHCO₃ and brine, dried over MgSO₄, filtered, then concentrated to give the crude product. Purification by flash chromatography on silica gel with CH₂Cl₂:MeOH (95:5) gave a white foam (0.37 g); TLC, $R_f$=0.55, silica gel, CH₂Cl₂:MeOH (95:5).

b. N-alpha-4-Phenylbenzoyl-N-epsilon-benzyloxycarbonyl-L-lysyl-L-valyl-L-prolyl-L-valinal The product of Example 26a was treated with p-toluenesulfonic acid as described in Example 10d to give a white foam (0.31 g); TLC, $R_f$=0.35, silica gel, MeOH:CH₂Cl₂ (5:95).

Elemental Analysis: Calculated for C₄₂H₅₃N₅O₇.0.5-H₂O: C, 67.35; H, 7.26; N, 9.35. Found: C, 67.11; H, 7.43; N, 9.16.

EXAMPLE 27

N-alpha-[2-(2-Pyridyl)-ethyloxycarbonyl]-N-epsilon-benzyloxy carbonyl-L-lysyl-L-valyl-L-prolyl-L-valinal Formula I: $R^1$=—CH(CH₃)₂; $R^2$=—CH(CH₃)₂; $R^3$=—(CH₂)₄NHCO₂CH₂C₆H₅; $R^4$=—O(CH₂)₂C₅H₄N a. N-alpha-[2-(2-Pyridyl)-ethyloxycarbonyl]-N-epsilon-benzyloxycarbonyl-L-lysyl-L-valyl-L-prolyl-L-valinal diethylacetal To a stirred solution of the product of Example 14f (400 mg, 0.63 mmol) in acetonitrile:H₂O (40 ml, 1:1) was added 2-(2-pyridyl)-ethyl p-nitrophenyl carbonate hydrochloride (208 mg, 0.64 mmol). When dissolution was complete, triethylamine (127 mg, 1.27 mmol) was added and the mixture was stirred at room temperature for 2 hr. The acetonitrile was removed under vacuum and the aqueous phase was diluted with water (20 ml) and extracted with EtOAc (2×200 ml). The combined extracts were dried (Na₂SO₄) and concentrated to yield the crude product. Purification by flash chromatography on silica gel with MeOH:CHCl₃ (5:95) gave the title compound (250 mg) as a white foam.

Elemental Analysis: Calculated for C₄₁H₆₂N₆O₉: C, 62.89; H, 7.98; N, 10.73. Found: C, 63.01; H, 8.07; N, 10.70.

b. N-alpha-8 2-(2-Pyridyl)-ethyloxycarbonyl]-N-epsilon-benzyloxycarbonyl-L-lysyl-L-valyl-L-prolyl-L-valinal A mixture of the product of Example 27a (240 mg, 0.31 mmol) and p-toluenesulfonic acid (117 mg, 0.62 mmol) in acetone (20 ml) was stirred for 3 hr. at room temperature. The solvent was removed under vacuum and the residue was dissolved in EtOAc. This solution was washed with aqueous 1N NaHCO₃ and dried (Na₂SO₄). Evaporation of the solvent gave a white foam (226 mg); TLC, $R_f$=0.30, silica gel, MeOH:CHCl₃ (6:94).

Elemental Analysis: Calculated for C₃₇H₅₂N₆O₈.-H₂O: C, 61.14; H, 7.48; N, 11.56. Found: C, 60.71; H, 7.44; N, 11.43.

EXAMPLE 28

N-alpha-N-epsilon-Dibenzoyl-L-lysyl-L-valyl-L-prolyl-L-valinal

Formula (I): $R^1$=—CH(CH₃)₂; $R^2$=—CH(CH₃)₂; $R^3$=—(CH₂)₄NHCOC₆H₅; $R^4$=—C₆H₅ a. N-alpha-N-epsilon-Dibenzoyl-L-lysyl-L-valyl-L-prolyl-L-valinal diethylacetal 1-(3-Dimethylaminopropyl)-3-ethyl carbodiimide hydrochloride (0.255 g, 1.18 mmol) and N-methylmorpholine (0.17 ml, 1.6 mmol) were added to a solution of the product of Example 13c (0.40 g, 1.07 mmol), N-alpha-N-epsilon dibenzoyl L-lysine (0.388 g, 1.07 mmol) and HOBT (0.289 g, 2.14 mmol) in $CH_2Cl_2$ (25 ml) at 0° C. under $N_2$ atmosphere. The reaction mixture was stirred at 0° C. for 1 hr. and then at room temperature overnight. The reaction mixture was concentrated and the oily residue was dissolved in EtOAc, washed with aqueous 1N HCl, brine, 5% aqueous $NaHCO_3$ and brine, dried over $MgSO_4$ and concentrated to give the crude product. This material was purified by flash chromatography on silica gel with $CH_2Cl_2$:MeOH (95:5) to give a white foam (0.58 g); TLC, $R_f$=0.55, silica gel, $CH_2Cl_2$:MeOH (95:5).

b.
N-alpha-N-epsilon-Dibenzoyl-L-lysyl-L-valyl-L-prolyl-L-valinal

The product of Example 28a was reacted with p-toluenesulfonic acid as described in Example 10d to give a white foam (0.56 g); TLC, $R_f$=0.45, silica gel, $CH_2Cl_2$:MeOH (95:5).

Elemental Analysis: Calculated for $C_{35}H_{47}N_5O_6.0.5$-$H_2O$: C, 65.39; H, 7.52; N, 10.89. Found: C, 65.27; H, 7.58; N, 10.71.

EXAMPLE 29

N-alpha-N-epsilon-Diacetyl-L-lysyl-L-valyl-L-prolyl-L-valinal

Formula (I): $R^1$=—$CH(CH_3)_2$; $R^2$=—$CH(CH_3)_2$; $R^3$=—$(CH_2)_4NHCOCH_3$; $R^4$=—$CH_3$ a.
N-alpha-N-epsilon-Diacetyl-L-lysyl-L-valyl-L-prolyl-L-valinal diethylacetal The title compound was prepared as in Example 28a, using 1-(3-dimethylaminopropyl)-3-ethyl carbodiimide hydrochloride (0.285 g, 1.5 mmol), N-methylmorpholine (0.22 ml, 2.03 mmol), the product of Example 13c (0.50 g, 1.35 mmol), N-alpha-N-epsilon-diacetyl-L-lysine (0.308 g, 1.35 mmol) and HOBT (0.365, 2.7 mmol) in THF (15 ml) and DMF (7 ml). The product was purified by flash chromatography with $CH_2Cl_2$:MeOH (9:1) to give an off-white foam (0.38 g); TLC, $R_f$=0.6, silica gel, $CH_2Cl_2$:MeOH (9:1).

b.
N-alpha-N-epsilon-Diacetyl-L-lysyl-L-valyl-L-prolyl-L-valinal

The product of Example 29a was treated with p-toluenesulfonic acid as described in Example 10d to give an off-white foam (0.29 g); TLC, $R_f$=0.5, silica gel, $CH_2Cl_2$:MeOH (85:15).

Elemental Analysis: Calculated for $C_{25}H_{43}N_5O_6.1.25H_2O$: C, 56.42; H, 8.61; N, 13.16. Found: C, 56.42; H, 8.51; N, 12.86.

EXAMPLE 30

N-Benzyloxycarbonyl-L-phenylalanyl-L-valyl-L-prolyl-L-valinal

Formula (I): $R^1$=—$CH(CH_3)_2$, $R^2$=—$CH(CH_3)_2$; $R^3$=—$CH_2C_6H_5$, $R^4$=—$OCH_2C_6H_5$ a.
N-Benzyloxycarbonyl-L-phenylalanyl-L-valyl-L-prolyl-L-valinal diethylacetal The title compound was prepared as in Example 1e, using a solution of N-benzyloxycarbonyl-L-phenlalanine (0.40 g, 1.35 mmol) and N-methylmorpholine (0.15 ml, 1.35 mmol) in dry THF (10 ml) and adding isobutyl chloroformate (0.17 ml, 1.35 mmol) followed by a solution the product of Example 13c (0.50 g, 1.35 mmol) in dry THF (10 ml). The crude product was purified by flash chromatography on silica gel with MeOH:$CHCl_3$ (2:98) to give the product (0.78 g); TLC, $R_f$=0.41, silica gel, MeOH:$CHCl_3$ (5:95).

b.
N-Benzyloxycarbonyl-L-phenylalanyl-L-valyl-L-prolyl-L-valinal p-Toluenesulfonic acid (160 mg, 0.84 mmol) was added to a solution of the product of Example 30a (0.38 g, 0.58 mmol) in acetone (100 ml) and the reaction was stirred for 2 hr. The reaction was concentrated under vacuum and the residue was dissolved in EtOAc (50 ml). This solution was washed with aqueous 5% $NaHCO_3$ and brine, dried over $Na_2SO_4$, filtered and concentrated under vacuum to give the product (0.29 g); TLC, $R_f$=0.29, silica gel, MeOH:$CHCl_3$ (5:95).

Elemental Analysis: Calculated for $C_{32}H_{42}N_4O_6.0.5$-$H_2O$: C, 65.40; H, 7.37; N, 9.53. Found: C, 65.76; H, 7.46; N, 9.22.

EXAMPLE 31

Preparation of Bisulfite Adducts of Formula (I) Aldehydes of the Invention

A solution of an aldehyde of the invention in MeOH:$H_2O$ (2:1 to 1:1, 5–10 ml/g of aldehyde) was treated with 2 equivalents of $NaHSO_3$ and stirred until dissolution was complete. The MeOH was removed under vacuum and the resulting aqueous solution was lyophilized to give the product as a white solid.

Bisulfite adducts of Formula (I) aldehydes prepared in this manner are shown in Table I.

TABLE I

Bisulfite Adducts of Formula I Compounds
$R^1 = R^2 =$ —$CH(CH_3)_2$

| Aldehyde from Example | $R^3$ | $R^4$ | Molecular Composition | Elemental Analysis Calculated | Found |
|---|---|---|---|---|---|
| 1f | b | —$OC(CH_3)_3$ | $C_{34}H_{53}N_5O_8.2NaHSO_3 2H_2O$ | C, 45.18 | 45.16 |
| | | | | H, 6.58 | 6.21 |
| | | | | N, 7.75 | 7.64 |
| | | | | S, 7.09 | 7.84 |
| 4d | a | —$OC(CH_3)_3$ | $C_{33}H_{52}N_6O_7.2NaHSO_3.2H_2O$ | C, 44.59 | 44.81 |
| | | | | H, 6.58 | 6.46 |
| | | | | N, 9.45 | 9.05 |
| 6k | b | —$(CH_2)_2CO_2H$ | $C_{33}H_{49}N_5O_9.2NaHSO_3$ | C, 44.67 | 45.69 |
| | | | | H, 5.92 | 5.88 |
| | | | | N, 8.07 | 7.88 |

TABLE I-continued

Bisulfite Adducts of Formula I Compounds
$R^1 = R^2 = -CH(CH_3)_2$

| Aldehyde from Example | $R^3$ | $R^4$ | Molecular Composition | Elemental Analysis Calculated | | Found |
|---|---|---|---|---|---|---|
| 8b | b | $-(CH_2)_2CO_2CH_3$ | $C_{34}H_{51}N_5O_9 \cdot 2NaHSO_3 \cdot 2H_2O$ | C, | 44.49 | 44.62 |
| | | | | H, | 6.26 | 5.96 |
| | | | | N, | 7.63 | 7.70 |
| | | | | S, | 6.99 | 7.39 |
| 10d | b | $-OCH_2C_6H_5$ | $C_{37}H_{51}N_5O_8 \cdot 2NaHSO_3$ | C, | 49.27 | 49.34 |
| | | | | H, | 5.92 | 5.98 |
| | | | | N, | 7.76 | 7.58 |
| 11f | c | $-(CH_2)_2CO_2H$ | $C_{25}H_{42}N_4O_7 \cdot 2NaHSO_3 \cdot 2H_2O$ | C, | 39.78 | 39.30 |
| | | | | H, | 6.41 | 5.89 |
| | | | | N, | 7.42 | 7.14 |
| 13g | d | $-(CH_2)_2CO_2CH_3$ | $C_{26}H_{44}N_4O_7 \cdot 2NaHSO_3$ | C, | 42.61 | 43.69 |
| | | | | H, | 6.32 | 6.43 |
| | | | | N, | 7.64 | 7.67 |
| 14h | b | $-CH_2NHCOCH_3$ | $C_{33}H_{50}N_6O_8 \cdot 2NaHSO_3 \cdot 2H_2O$ | C, | 43.90 | 43.28 |
| | | | | H, | 6.25 | 5.86 |
| | | | | N, | 9.31 | 8.94 |
| 18c | b | $-C(CH_3)_3$ | $C_{34}H_{53}N_5O_7 \cdot 2NaHSO_3$ | C, | 47.93 | 47.83 |
| | | | | H, | 6.50 | 6.46 |
| | | | | N, | 8.22 | 8.14 |
| 23b | b | $C_6H_3Cl_2$ | $C_{36}H_{47}N_5Cl_2O_7 \cdot 2NaHSO_3 \cdot H_2O$ | C, | 45.09 | 45.02 |
| | | | | H, | 5.36 | 5.35 |
| | | | | N, | 7.30 | 6.99 |
| 26b | b | $C_6H_4C_6H_5$ | $C_{42}H_{53}N_5O_6 \cdot 2NaHSO_3$ | C, | 53.21 | 53.35 |
| | | | | H, | 5.85 | 5.97 |
| | | | | N, | 7.38 | 7.41 |
| 28b | e | $C_6H_5$ | $C_{35}H_{47}N_5O_7 \cdot 2NaHSO_3 \cdot H_2O$ | C, | 48.90 | 49.14 |
| | | | | H, | 5.97 | 5.86 |
| | | | | N, | 8.14 | 8.03 |

Notes:
a - $R^3 = -(CH_2)_4NHCONHC_6H_5$
b - $R^3 = -(CH_2)_4NHCO_2CH_2C_6H_5$
c - $R^3 = -CH_2CH(CH_3)_2$
d - $R^3 = -(CH_2)_3CH_3$
e - $R^3 = -(CH_2)_4NHCOC_6H_5$

EXAMPLE 32

N-[1(S)-Carbomethoxy-3-methylbutyl]carbamoyl-L-valyl-L-prolyl-L-valinal

Formula (II): $R^5 = -CH(CH_3)_2$; $R^6 = -CH(CH_3)_2$; $R^7 = -CH_2CH(CH_3)_2$; $R^8 = -OCH_3$.

a. N-alpha-t-Butyloxycarbonyl-L-valyl-L-proline benzyl ester

The title compound was prepared as in Example 1a, using a solution of N-alpha-t-butyloxycarbonyl-L-valine (5.0 g, 23 mmol) in DMF (80 ml) cooled to 0° C. and adding successively DCC (5.15 g, 25 mmol), HOBT (6.21 g, 46 mmol) and a slurry of L-proline benzyl ester (5.56 g, 23 mmol) in TEA (3.4 ml, 23 mmol) and DMF (20 ml). The crude yellow oil was dissolved in EtOAc (200 ml) and the solution washed successively with 20% aqueous citric acid (200 ml), saturated aqueous NaHCO$_3$, aqueous 1N HCl and brine. The organic layer was dried over Na$_2$SO$_4$, filtered and concentrated under vacuum to give the crude product as a yellow oil. Purification by flash chromatography on silica gel with EtOAc:CH$_2$Cl$_2$ (5:95) followed by EtOAc:CH$_2$Cl$_2$ (1:9) gave the product (7.36 g); TLC, R$_f$=0.57, silica gel, EtOAc:CH$_2$Cl$_2$ (1:4).

b. L-Valyl-L-proline benzyl ester hydrochloride

The title compound was prepared as in Example 1b using a solution of the product of Example 32a (5.0 g, 12.4 mmol) in EtOAc (20 ml) and adding 6N HCl/EtOAc (20 ml) to give a solid residue which was triturated with petroleum ether and filtered under N$_2$ to yield the purified product (4.1 g) as a white solid.

c. L-Leucine methyl ester isocyanate

A three-neck 1 liter round bottom flask, fitted with gas inlet, mechanical stirrer, reflux condenser and gas outlet connected to a 30% aqueous NaOH trap was charged with L-leucine methyl ester hydrochloride (61.0 g, 0.336 mmol) and dry toluene (250 ml). The mixture was heated to gentle reflux for 0.5 hr. while a vigorous stream of phosgene was continuously introduced. Following dissolution of the solids (0.5 hr.) phosgene was introduced for an additional 15 min. The product was isolated by initially removing the toluene under vacuum and fractionally distilling the remaining residue under vacuum to give the product (48.0 g), bp=71°–73° C. at 0.8 torr.

d. N-[1(S)-Carbomethoxy-3-methylbutyl]carbamoyl-L-valyl-L-proline benzyl ester N-Methylmorpholine (6.0 ml, 54.5 mmol) and a solution of the product of Example 32c (10.0 g, 58.5 mmol) in CHCl$_3$ (50 ml) was added to a solution of the product of Example 32b (18.57 g, 54.5 mmol) in CHCl$_3$ (250 ml) cooled to 0° C. The solution was stirred for 2 hr. and the solvent removed under vacuum. The residue was dissolved in EtOAc (200 ml) and washed successively with saturated aqueous NaHCO$_3$, H$_2$O, aqueous 1N HCl, and brine. The organic layer was dried with Na$_2$SO$_4$, filtered and concentrated under vacuum to give the crude product (27.54 g) as a white foam. Purification using a Waters Prep 500 ® Liquid Chromatograph with hexan:Et$_2$O (1:3) as eluent gave the desired product (20.87 g); TLC, R$_f$=0.57, silica gel, Et$_2$O.

Elemental Analysis: Calculated for $C_{25}H_{37}N_3O_6$: C, 63.14; H, 7.84; N, 8.84. Found: C, 63.32; H, 7.99; N, 8.59.

e.

N-[1(S)-Carbomethoxy-3-methylbutyl]carbamoyl-L-valyl-L-proline

A solution of the product of Example 32d (5.16 g) and 10% Pd/C (1.0 g) in ethanol (100 ml) was hydrogenated using a Parr shaker (3 atm. $H_2$) for 3 hr. The reaction mixture was filtered through Celite ® and the filtrate concentrated under vacuum to give a gummy residue which was triturated with hexane to yield the product (3.54 g) as a white solid.

Elemental Analysis:
Calculated for $C_{18}H_{31}N_3O_6$: C, 56.09; H, 8.11; N, 10.90. Found: C, 55.51; H, 7.91; N, 10.68.

f.

N-[1(S)-Carbomethoxy-3-methylbutyl]carbamoyl-L-valyl-L-prolyl-L-valinol

The title compound was prepared as in Example 1e using a solution of the product of Example 32e (2.0 g, 5.2 mmol) in dry THF (30 ml) and adding N-methylmorpholine (0.57 ml, 5.2 mmol), isobutyl chloroformate (0.68 ml, 5.2 mmol) and a solution of L-valinol (0.535 g, 5.2 mmol) in dry THF (10 ml) to give the crude product (2.38 g) which was used without further purification; TLC, $R_f$=0.44, silica gel, MeOH:CHCl$_3$ (1:9).

g.

N-[1(S)-Carbomethoxy-3-methylbutyl]carbamoyl-L-valyl-L-prolyl-L-valinal

The title compound was prepared as in Example 1f using oxalyl chloride (0.25 ml, 2.85 mmol), in $CH_2Cl_2$ (4 ml) and adding DMSO (0.4 ml, 5.7 mmol) in $CH_2Cl_2$ (1 ml), the product of Example 32f (0.9 g, 1.9 mmol) in $CH_2Cl_2$ (2 ml) and TEA (0.8 ml, 5.7 mmol). The crude mixture was purified using three successive flash column chromatographies on silica gel with MeOH:CHCl$_3$ (5:95), MeOH:CHCl$_3$ (2.5:97.5), and EtOAc:Et$_2$O (1:1) respectively as eluents to give the product (0.625 g); TLC, $R_f$=0.37, silica gel, MeOH:CHCl$_3$ (5:95).

Elemental Analysis: Calculated for $C_{23}H_{40}N_4O_6$: C, 58.95; H, 8.60; N, 11.96. Found: C, 58.79; H, 8.77; N, 12.14.

h.

N-[1(S)-Carbomethoxy-3-methylbutyl]carbamoyl-L-valyl-L-prolyl-L-valinal bisulfite A solution of the product of Example 32g (0.515 g, 1.1 mmol) and NaHSO$_3$ (0.229 g, 2.2 mmol) in MeOH:H$_2$O (1:1) (10 ml) was stirred at room temperature until dissolution was complete. The product (0.7 g) was isolated by removing the MeOH under vacuum and the $H_2O$ using a lyophilizer.

Elemental Analysis: Calculated for $C_{23}H_{40}N_4O_6$·2NaHSO$_3$·3H$_2$O: C, 39.76; H, 6.38; N, 8.07. Found: C, 39.89; H, 6.22; N, 8.06.

EXAMPLES 33–35

Formula (II): $R^5$=see table; $R^6$=—CH(CH$_3$)$_2$; $R^7$=CH$_2$CH(CH$_3$)$_2$; $R^8$=—OCH$_3$.

In a manner analogous to that described in Example 32, steps f and g, the product of Example 32e was converted to the compounds of Table II by use of the appropriate amino alcohol containing the substituent $R^5$.

TABLE II

| Example | $R^5$ | Formula | | Elemental Analysis | | $R_f$ |
|---|---|---|---|---|---|---|
| | | | | Calc'd | Found | |
| 33 | —CH(CH$_3$)CH$_2$CH$_3$ | $C_{24}H_{42}N_4O_6$·0.5H$_2$O | C, | 58.63 | 58.59 | 0.51 |
| | | | H, | 8.82 | 8.47 | |
| | | | N, | 11.40 | 11.47 | |
| 34 | D,L-(CH$_2$)$_2$CH$_3$ | $C_{23}H_{40}N_4O_6$·H$_2$O | C, | 56.77 | 56.48 | 0.49 |
| | | | H, | 8.69 | 8.44 | |
| | | | N, | 11.51 | 11.20 | |
| 35 | —(CH$_2$)$_2$CH$_3$ | $C_{23}H_{40}N_4O_6$·H$_2$O | C, | 56.77 | 57.15 | 0.48 |
| | | | H, | 8.69 | 8.34 | |
| | | | N, | 11.51 | 11.50 | |

All $R_f$ values in Table II were obtained by TLC on silica gel, using EtOAc as eluent.

EXAMPLE 36

N-alpha-t-Butyloxycarbonyl-N-epsilon-benzyloxycarbonyl-L-lysyl-L-prolyl-L-valinal Formula (III): $R^9$=—CH(CH$_3$)$_2$; $R^{10}$=—(CH$_2$)$_4$NHCOOCH$_2$C$_6$H$_5$; $R^{11}$=—OC(CH$_3$)$_3$.

a.

N-alpha-t-butyloxycarbonyl-N-epsilon-benzyloxycarbonyl-L-lysyl-L-proline methyl ester Isobutyl chloroformate (0.13 ml, 1.0 mmol) was added dropwise to a solution of N-alpha-t-butyloxycarbonyl-N-epsilonbenzyloxycarbonyl-L-lysine and N-methylmorpholine (0.12 ml, 1.1 mmol) in THF (8.0 ml) cooled to −23° C. under $N_2$. The reaction mixture was stirred for 20 min. and the solution cooled to −50° C. A solution of L-proline methyl ester hydrochloride and N-methylmorpholine (0.12 ml, 1.1 mmol) in DMF (2 ml) was added in one portion and the reaction mixture was allowed to warm slowly to room temperature and was stirred overnight. The solution was filtered, concentrated under vacuum and the residue dissolved in EtOAc (100 ml). The EtOAc solution was washed with 1N aqueous HCl, saturated NaHCO$_3$, and brine. The organic layer was dried over Na$_2$SO$_4$, filtered and concentrated under vacuum to give the crude product which was purified by flash chromatography using Et$_2$O as the eluent to give the final product (0.36 g); TLC, $R_f$=0.44, silica gel, Et$_2$O.

b.

N-t-Butyloxycarbonyl-N-epsilon-benzyloxycarbonyl-L-lysyl-L-proline

A solution of the product of Example 36a (0.36 g, 0.73 mmol) in MeOH (2.5 ml) and 1N aqueous NaOH (1.0 ml) was stirred at room temperature for 5 hr. The solution was concentrated under vacuum and the residue dissolved in H$_2$O (10 ml) and extracted with Et$_2$O. The aqueous layer was acidified with 10% citric acid whereupon a white solid precipitated. The solid was extracted into EtOAc and the organic layer dried with Na$_2$SO$_4$ and concentrated under vacuum to give the product (0.25 g); TLC, R$_f$=0.7, silica gel, MeOH:CHCl$_3$:HOAc (9.5:90:0.5).

c. N-t-Butyloxycarbonyl-N-epsilon-benzyloxycarbonyl-L-lysyl-L-prolyl-L-valinol Isobutyl chloroformate (70 ml, 0.52 mmol) was added dropwise to a solution of the product of Example 36b (0.25 g, 0.52 mmol) and N-methylmorpholine (60 ml, b 0.55 mmol) in THF (6 ml) cooled to −20° C. under a nitrogen atmosphere. The reaction mixture was stirred for 15 min. and the solution cooled to −45° C. A solution of L-valinol (0.054 g, 0.52 mmol) in THF (2 ml) was added, the reaction mixture stirred for 2 hr. and the solution was allowed to warm to room temperature and was stirred overnight. The reaction mixture was concentrated under vacuum and the residue dissolved in EtOAc. The solution was washed successively with 1N aqueous HCl, saturated NaHCO$_3$ and brine. The organic layer was dried with Na$_2$SO$_4$, filtered and concentrated under vacuum to give the product (0.26 g) as a white foam; TLC, R$_f$=0.45, silica gel, MeOH:CHCl$_3$ (5:95).

d. N-t-Butyloxycarbonyl-N-epsilon-benzyloxycarbonyl-L-lysyl-L-prolyl-L-valinal The title compound was prepared as in Example 1f using oxalyl chloride (0.44 g, 3.5 mmol) in CH$_2$Cl$_2$ (40 ml) and successively adding DMSO (0.68 g, 8.75 mmol) in CH$_2$Cl$_2$ (7 ml), the product of Example 36c (0.90 g, b 1.6 mmol) in CH$_2$Cl$_2$ (7 ml) and TEA (0.68 g, 6.73 mmol) to give the crude product. Purification by flash chromatography on silica gel with MeOH:Et$_2$O (4:96) gave the product (1.50 g); TLC, R$_f$=0.54, silica gel, MeOH:Et$_2$O (4:96).

Elemental Analysis: Calculated for C$_{29}$H$_{44}$N$_4$O$_7$.H$_2$O: C, 60.19; H, 8.01; N, 9.68. Found: C, 60.40; H, 7.68; N, 9.60.

e. N-t-Butyloxycarbonyl-N-epsilon-benzyloxycarbonyl-L-lysyl-L-prolyl-L-valinal bisulfite A solution of the product of Example 36d (1.51 g, 2.69 mmol) and NaHSO$_3$ (0.59 g, 5.65 mmol) in MeOH (15 ml) and H$_2$O (8 ml) was stirred until dissolution was complete. The MeOH was removed under vacuum and the H$_2$O removed with a lyophilizer to give the product (1.75 g).

Elemental Analysis: Calculated for C$_{29}$H$_{44}$N$_4$O$_7$.2NaHSO$_3$: C, 45.31; H, 6.03; N, 7.29. Found: C, 45.45; H, 5.87; N, 7.30.

EXAMPLE 37

N-t-Butyloxycarbonyl-L-valyl-L-prolyl-L-valinal

Formula (III): R$^9$=—CH(CH$_3$)$_2$; R$^{10}$=—CH(CH$_3$)$_2$; R$^{11}$=—OC(CH$_3$)$_3$.

a. N-t-Butyloxycarbonyl-L-valyl-L-proline

A mixture of the product of Example 32a (7.25 g, 17.9 mmol) and 10% Pd/C (1.4 g) in ethanol (150 ml) was stirred under 3 atmospheres of H$_2$ at room temperature for 2 hr. The reaction mixture was filtered through Celite ® and the filtrate concentrated under vacuum to give the desired product (5.68 g).

b. N-t-Butyloxycarbonyl-L-valyl-L-prolyl-L-valinol

Isobutyl chloroformate (1.25 ml, 9.6 mmol) was added to a solution of the product of Example 37a (3.0 g, 9.6 mmol) and N-methylmorpholine (1.05 ml, 9.6 mmol) in THF (40 ml). A solution of L-valinol (0.99 g, 9.6 mmol) in THF (40 ml) was added to give the title product (3.16 g); TLC, R$_f$=0.33, silica gel, EtOAc.

c. N-t-Butyloxycarbonyl-L-valyl-L-prolyl-L-valinal

A solution of the product of Example 37b (0.5 g, 0.78 mmol) in CH$_2$Cl$_2$ (1 ml) was added to a solution of pyridinium chlorochromate (0.445 g, 2.2 mmol) in dry CH$_2$Cl$_2$ (3 ml). The reaction mixture was stirred at room temperature until the reaction was complete by TLC (R$_f$=0.8, silica gel, EtOAc). Dry Et$_2$O was added to the reaction mixture and the solution decanted. The black tarry residue was triturated with Et$_2$O and the solutions combined and filtered through a Florisil ® column to give the title product (0.100 g). (Florisil ® is a registered trademark of Floridin Co., Berkeley Springs, W. Va., U.S.A., for activated magnesium silicate in the form of hard porous stable white granules. This material is useful as an analytical reagent, adsorbent and catalyst).

Elemental Analysis: Calculated for C$_{20}$H$_{35}$N$_3$O$_5$.0.5-H$_2$O: C, 59.09; H, 8.92; N, 10.33. Found: C, 59.13; H, 8.77; N, 9.98.

EXAMPLE 38

N-Succinyl-L-valyl-L-prolyl-L-valinal

Formula (III): R$^9$=—CH(CH$_3$)$_2$; R$^{10}$=—CH(CH$_3$)$_2$; R$^{11}$=—(CH$_2$)$_2$COOH.

a. L-Valyl-L-prolyl-L-valinol

Trifluoroacetic acid (3.4 ml, 44 mmol) was added to a solution of the product of Example 37b (1.76 g, 4.4 mmol) in CH$_2$Cl$_2$ (3.4 mmol) at room temperature and the mixture was stirred for 1 hr. The reaction mixture was cooled to 0° C. and a solution of Na$_2$CO$_3$ (2.6 g, 50 mmol) in H$_2$O (10 ml) was added dropwise. The reaction mixture was diluted with CH$_2$Cl$_2$ and the organic layer separated, dried over Na$_2$SO$_4$ and filtered to give the title product (0.93 g) as a hygroscopic solid.

b. N-Succinyl-L-valyl-L-prolyl-L-valinol

A solution of succinic anhydride (0.31 g, 3.1 mmol) in CH$_3$CN was added to a solution of the product of Example 38a (0.83 g, 2.8 mmol) in CH$_3$CN (30 ml) at room temperature. The reaction mixture was stirred overnight and the solution concentrated under vacuum to give the crude product. Purification by flash chromatography on silica gel with MeOH:CHCl$_3$:HOAc (4.5:95:0.5) gave the product (0.620 g) as a white solid; TLC, R$_f$=0.24, silica gel, MeOH:CHCl$_3$:HOAc (4.5:95:0.5).

c. N-Succinyl-L-valyl-L-prolyl-L-valinal

A solution of DMSO (0.35 ml, 5.0 mmol) in CH$_2$Cl$_2$ (1.0 ml) was added to a solution of oxalyl chloride (0.22 ml, 2.5 mmol) in CH$_2$Cl$_2$ cooled to −23° C. under a nitrogen atmosphere. A solution of the product of Example 38b (0.5 g, 1.25 mmol) in CH$_2$Cl$_2$ (3 ml) was added dropwise. The reaction mixture was stirred for 15 min. and TEA (0.69 ml, 5.0 mmol) was added dropwise. The reaction mixture was allowed to warm to room temperature and was diluted with CH$_2$Cl$_2$. The solution was washed with 10% aqueous AcOH and brine, dried over Na$_2$SO$_4$, filtered and concentrated to give the crude product (0.750 g) as a yellow oil. The oil was purified by flash chromatography on silica gel with MeOH:CHCl$_3$:HOAc (4.5:95:0.5) to give the final product (0.042 g); TLC, R$_f$=0.33, silica gel, MeOH:CHCl$_3$:HOAc (9.5:90:0.5).

EXAMPLE 39

N-Acetyl-L-valyl-L-prolyl-L-valinal

Formula (III): R$^9$=—CH(CH$_3$)$_2$; R$^{10}$=—CH(CH$_3$)$_2$; R$^{11}$=—CH$_3$;

a. N-Acetyl-L-valyl-L-prolyl-L-valinal diethylacetal

Acetyl chloride (0.41 g, 5.19 mmol) was added to a solution of the product of Example 13c (1.91 g, 5.19 mmol) in CH$_2$Cl$_2$ (50 ml) and N-methylmorpholine (3 ml) at 0° C. under a nitrogen atmosphere. The reaction mixture was stirred for 15 min. and then warmed to room temperature. Water (20 ml) was added. The organic layer was washed successively with 20% citric acid, brine, saturated aqueous NaHCO$_3$ and brine and dried over MgSO$_4$, filtered and concentrated to give a viscous oil. The product was purified by flash chromatography on silica gel with CH$_2$Cl$_2$:MeOH (98:2) to give an oil (1.3 g). TLC, R$_f$=0.5 silica gel CH$_2$Cl$_2$:MeOH (95:5).

Elemental Analysis: Calculated for C$_{21}$H$_{39}$N$_3$O$_5$: C, 60.99; H, 9.50; N, 10.16. Found: C, 60.55; H, 9.42; N, 10.17.

b. N-Acetyl-L-valyl-L-prolyl-L-valinal

Dowex ®50WX-H resin (40 ml) was added to a solution of the product of Example 39a (1.15 g, 2.78 mmol) in H$_2$O (40 ml) and acetone (5 ml) at room temperature under a nitrogen atmosphere and the mixture was stirred for 20 hr. The mixture was filtered and the resin was washed with acetone. The filtrate and wash were combined and concentrated in vacuo to remove the acetone. Water was removed with a lyophilizer to give the product as a white powder (0.757 g).

Elemental Analysis: Calculated for C$_{17}$H$_{29}$N$_3$O$_4$.0.4-H$_2$O: C, 58.90; H, 8.66; N, 12.10. Found: C, 58.93; H, 8.44; N, 11.97.

EXAMPLE 40

N-Benzyloxycarbonyl-L-valyl-L-prolyl-L-valinal

Formula III: R$^9$=—CH(CH$_3$)$_2$; R$^{10}$=—CH(CH$_3$)$_2$; R$^{11}$=—OCH$_2$C$_6$H$_5$ a. N-Benzyloxycarbonyl-L-valyl-L-prolyl-L-valinal A mixture of p-toluenesulfonic acid (150 mg) and the product of Example 13b (500 mg, 0.988 mmol) in acetone (70 ml) was stirred at room temperature for 3 hr. The mixture was concentrated under vacuum and the residue was dissolved in EtOAc. This solution was washed with 5% aqueous NaHCO$_3$ and brine, dried over MgSO$_4$, filtered and concentrated to give a glass (410 mg); TLC, R$_f$=0.60, silica gel, CH$_2$Cl$_2$:MeOH (95:5).

b. N-Benzyloxycarbonyl-L-valyl-L-prolyl-L-valinal bisulfite adduct

The product of Example 40a was treated as described in Example 32h to provide a white powder.

Elemental Analysis: Calculated for C$_{23}$H$_{33}$N$_3$O$_5$.-2NaHSO$_3$: C, 43.18; H, 5.52; N, 6.56. Found: C, 42.85; H, 5.64; N, 6.43.

What is claimed is:

1. A proline derivative of the following formula (I), (II) or (III):

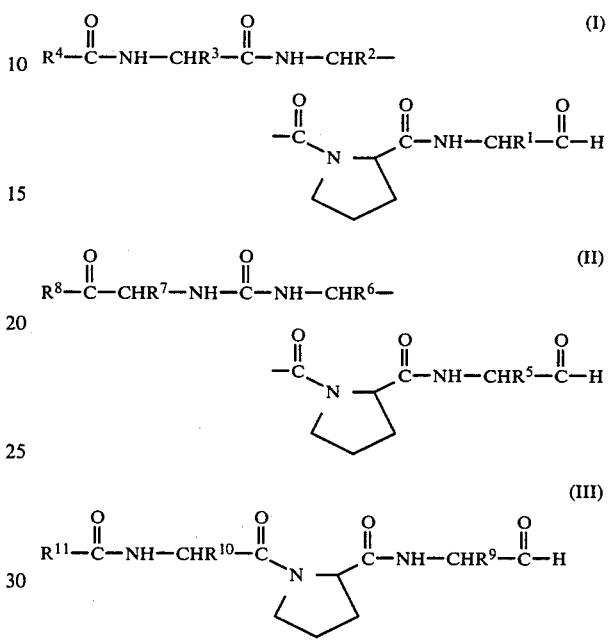

wherein
R$^1$, R$^5$ and R$^9$ are lower alkyl groups containing from 3 to about 6 carbon atoms;
R$^2$, R$^3$, R$^6$, R$^7$ and R$^{10}$ are alkyl groups of about 1 to 10 carbon atoms which may optionally be substituted by a monocyclic aryl group or by an amide, urea or carbamate group via the nitrogen thereof; and
R$^4$ and R$^{11}$ are lower alkyl, substituted lower alkyl, lower alkoxy or substituted lower alkoxy groups wherein the alkyl or alkoxy contains about 1 to 6 carbon atoms, or monocyclic or bicyclic aryl groups; and
R$^8$ is hydroxy, a lower alkoxy group containing about 1 to 6 carbon atoms, or an aralkoxy group containing about 7 to 12 carbon atoms;
and wherein —CHR$^2$—, —CHR$^3$—, —CHR$^6$—, —CHR$^7$—, —CHR$^{10}$— and the proline group are of the L-configuration; or a pharmaceutically-acceptable acid- or base-addition salt thereof or a pharmaceutically-acceptable equilibrium addition compound of the aldehyde group thereof.

2. A proline derivative according to claim 1, wherein
R$^1$, R$^5$ and R$^9$ are lower alkyl groups containing 3 to 4 carbon atoms;
R$^2$, R$^3$, R$^6$, R$^7$ and R$^{10}$ are alkyl groups of 1 to 10 carbon atoms which may optionally be substituted by an amide, urea or carbamate group via the nitrogen thereof;
R$^4$ and R$^{11}$ are alkoxy groups of 1 to 6 carbon atoms, phenyl-(C$_{1-6}$-alkoxy) groups, carboxy-(C$_{1-6}$-alkyl) groups or (C$_{1-6}$-alkoxy)carbonyl-(C$_{1-6}$-alkyl) groups; and
R$^8$ is a hydroxy group, a lower alkoxy group of 1 to 6 carbon atoms, or a phenyl-(C$_{1-6}$-alkoxy) group;

or a pharmaceutically-acceptable acid- or bas-addition salt thereof, or a pharmaceutically-acceptable equilibrium addition compound of the aldehyde group thereof.

3. A proline derivative according to claim 1, wherein $R^2$ and $R^6$ are alkyl groups containing from 3 to about 6 carbon atoms which may optionally be substituted by a monocyclic aryl radical, $R^4$ and $R^{11}$ are lower alkyl groups from 1 to about 6 carbon atoms which may optionally be substituted by a monocyclic aryl radical; a substituted $C_{1-6}$ alkyl group in which the substituent is carboxy, $C_{1-6}$-alkoxycarbonyl, acetamido or lower alkanesulfonamidocarbonyl; or a phenyl, halophenyl or biphenylyl group; and $R^8$ is a hydroxy group, a lower alkoxy group containing about 1 to 6 carbon atoms, or an aralkoxy group containing about 7 to 12 carbon atoms;

or a pharmaceutically-acceptable acid- or base-addition salt thereof, or a pharmaceutically-acceptable equilibrium addition compound of the aldehyde group thereof.

4. A proline derivative according to claim 1 wherein:

$R^1$, $R^5$ and $R^9$ are branched chain alkyl groups of 3 to 4 carbon atoms;

$R^2$ and $R^6$ are alkyl groups of 3 to 4 carbon atoms or benzyl;

$R^3$ is an alkyl group of 3 to about 6 carbon atoms which may optionally be substituted by an amide, urea or carbamate group via the nitrogen thereof;

$R^4$ is a lower alkoxy group containing from 1 to about 6 carbon atoms which may optionally be substituted by a monocyclic aryl radical; a substituted $C_{1-6}$ alkyl group in which the substituent is carboxy, $C_{1-6}$-alkoxycarbonyl, acetamido or lower alkanesulfonamidocarbonyl; or a phenyl, halophenyl or biphenylyl group;

$R^7$ is a lower alkyl group of 1 to about 6 carbon atoms;

$R^8$ is a hydroxy group, a lower alkoxy group containing from 1 to about 6 carbon atoms, or an aralkoxy group containing about 7 to 12 carbon atoms;

$R^{10}$ is an alkyl group containing 3 to about 6 carbon atoms which may optionally be substituted by a monocyclic aryl radical; and $R^{11}$ is a monocyclic aryl-substituted alkoxy group in which the alkoxy contains 1 to about 4 carbon atoms, or a pharmaceutically-acceptable acid- or base-addition salt thereof or a pharmaceutically-acceptable equilibrium addition compound of the aldehyde group thereof.

5. A proline derivative according to claim 4, said proline derivative being of the formula (I).

6. A proline derivative according to claim 1, in which —$CHR^1$—, —$CHR^5$—, and —$CHR^9$— are of the L-configuration.

7. A proline derivative according to claim 1, said derivative being a compound selected from the group consisting of:

(a) N-alpha-succinyl-N-epsilon-benzyloxycarbonyl-L-lysyl-L-valyl-L-prolyl-L-valinal, (b) N-acetylglycyl-N-epsilon-benzyloxycarbonyl-L-lysyl-L-valyl-L-prolyl-L-valinal, (c) N-benzyloxycarbonyl-L-norleucyl-L-valyl-L-prolyl-L-valinal, (d) N-alpha-[3-(methylsulfonylaminocarbonyl)propionyl]-N-epsilon-benzyloxycarbonyl-L-lysyl-L-valyl-L-prolyl-L-valinal, (e) N-alpha-succinyl-N-epsilon-benzyloxycarbonyl-L-lysyl-L-phenylalanyl-L-prolyl-L-valinal, (f) N-alpha-(2,4-dichlorobenzoyl)-N-epsilon-benzyloxycarbonyl-L-lysyl-L-valyl-L-prolyl-L-valinal, (g) N-alpha-glutaryl-N-epsilon-benzyloxycarbonyl-L-lysyl-L-valyl-L-prolyl-L-valinal, (h) N-alpha-succinyl-N-epsilon-(2,4-dichlorobenzoyl)-L-lysyl-L-valyl-L-prolyl-L-valinal, and (i) N-alpha-(4-phenylbenzoyl)-N-epsilon-benzyloxycarbonyl-L-lysyl-L-valyl-L-prolyl-L-valinal, or a pharmaceutically-acceptable base-addition salt thereof or a pharmaceutically-acceptable equilibrium addition compound of the aldehyde group thereof.

8. A proline derivative according to claim 7, said derivative being N-alpha-succinyl-N-epsilon-benzyloxycarbonyl-L-lysyl-L-valyl-L-prolyl-L-valinal, or a pharmaceutically-acceptable base-addition salt thereof or an equilibrium addition compound of the aldehyde group thereof.

9. A base addition salt of a proline derivative according to claim 1, which is a sodium or potassium salt.

10. An equilibrium addition compound of a proline derivative according to claim 1, which is a bisulfite addition product.

11. A pharmaceutical composition useful in the treatment of pulmonary emphysema, atherosclerosis, and osteo- or rheumatoid arthritis comprising a pharmaceutically effective amount of a compound as claimed in claim 1 and a non-toxic pharmaceutically-acceptable diluent or carrier.

12. A composition according to claim 11, said composition being in the form of a liquid or powdered aerosol.

13. A method for the treatment of pulmonary emphysema in a warm-blooded animal in need of such treatment, which comprises administering to said animal a pharmaceutically effective amount of a compound according to claim 1.

14. A method according to claim 13 in which said composition is administered parenterally.

15. A method for the treatment of atherosclerosis in a warm-blooded animal in need of such treatment, which comprises administering to said animal a pharmaceutically effective amount of a compound according to claim 1.

16. A method for the treatment of arthritis in a warm-blooded animal in need of such treatment, which comprises administering to said animal a pharmaceutically effective amount of a compound according to claim 1.

* * * * *